US008349610B2

(12) United States Patent
Stewart et al.

(10) Patent No.: US 8,349,610 B2
(45) Date of Patent: Jan. 8, 2013

(54) METHODS, SYSTEMS AND DEVICES FOR ANALYZING A SURFACTANT-TREATED BIOLOGICAL FLUID SAMPLE

(75) Inventors: Ray F. Stewart, Belmont, CA (US); Kathryn M. Morton, Palo Alto, CA (US); Aaron Dickerman-Stewart, Redwood City, CA (US); Nathan Mak, San Francisco, CA (US)

(73) Assignee: Cantimer, Inc., Menlo Park, CA (US)

( * ) Notice: Subject to any disclaimer, the term of this patent is extended or adjusted under 35 U.S.C. 154(b) by 41 days.

(21) Appl. No.: 12/736,888

(22) PCT Filed: May 20, 2009

(86) PCT No.: PCT/US2009/003147
§ 371 (c)(1),
(2), (4) Date: Nov. 19, 2010

(87) PCT Pub. No.: WO2009/142743
PCT Pub. Date: Nov. 26, 2009

(65) Prior Publication Data
US 2011/0076775 A1    Mar. 31, 2011

Related U.S. Application Data

(60) Provisional application No. 61/128,217, filed on May 20, 2008.

(51) Int. Cl.
*G01N 33/487* (2006.01)
*G01N 33/48* (2006.01)
*G01N 33/50* (2006.01)
*B01J 19/00* (2006.01)

(52) U.S. Cl. .................. 436/2; 436/63; 436/74; 436/86; 436/95; 436/98; 436/108; 436/148; 436/149; 436/151; 436/163; 436/164

(58) Field of Classification Search ................ 436/2, 63, 436/71, 73, 74, 148, 149, 151, 163, 164, 436/95, 98, 106, 108, 129, 86, 133, 182; 422/68.1, 82.01, 82.02, 82.13
See application file for complete search history.

(56) References Cited

U.S. PATENT DOCUMENTS

| 2002/0139936 | A1* | 10/2002 | Dumas ........................ 250/458.1 |
| 2005/0164299 | A1 | 7/2005 | Stewart |
| 2007/0249059 | A1 | 10/2007 | Stewart |
| 2009/0024060 | A1* | 1/2009 | Darrigrand et al. ............ 600/584 |
| 2010/0143196 | A1* | 6/2010 | Reed et al. .................. 422/82.02 |

FOREIGN PATENT DOCUMENTS

| EP | 1396726 A | 3/2004 |
| WO | WO 2008/040126 A | 4/2008 |

OTHER PUBLICATIONS

Database Biosis, Biosciences Information Service, Database Accession No. PREV198375016615, Granneman, et al., "A very precise high performance liquid chromatographic procedure for the determination of cefmenoxime, a new cephalosporin antibiotic in plasma", J. Chromatogr., vol. 229, No. 1, pp. 49-157 (1982) *Abstract.*
Database Medline, U.S. National Library of Medicine, Database Accession No. NLM1150764, Mondino, et al., "A new approach for obtaining total tryptophan recovery in plasma samples deproteinized with sulphosalicylic acid", J. Chromatogr., vol. 14, No. 2, pp. 297-302 (1975) *Abstract.*
Database Biosis, Biosciences Information Service, Database Accession No. PREV200100411862, Peng, et al., "Influence of specimen processing method on mycobacterium tuberculosis detection by PCR-reversed dot hybridization", Zhonghua diehe He Huxi Zazhi, vol. 24, No. 5, pp. 306-308 (2001) *Abstract.*
International Search Report from related PCT Patent Application No. PCT/US2009/003147 mailed on Oct. 12, 2009, now sublished as WO 2009/142743 A1 on Nov. 26, 2009.
Stewart, et al., "Human hydration level monitoring using embedded piezoresistive microcantilever sensors", Med. Eng. Phys., vol. 29, No. 10, pp. 1084-1088 (2007).

\* cited by examiner

*Primary Examiner* — Maureen Wallenhorst
(74) *Attorney, Agent, or Firm* — Judy M. Mohr; Jacqueline F. Mahoney; McDermott Will & Emery LLP

(57) ABSTRACT

Devices, methods and systems effective to evaluate a physical or chemical property of a surfactant-treated biological fluid sample are provided.

21 Claims, 12 Drawing Sheets

METHODS, SYSTEMS AND DEVICES FOR ANALYZING A SURFACTANT-TREATED BIOLOGICAL FLUID SAMPLE

CROSS REFERENCE TO RELATED APPLICATIONS

This application is a U.S. National Stage of International Patent Application No. PCT/US2009/003147, filed May 20, 2009, which claims the benefit of U.S. Provisional Application Ser. No. 61/128,217, filed May 20, 2008, all of which are hereby incorporated by reference.

TECHNICAL FIELD

The present subject matter relates to methods, systems and devices effective to measure a physical or chemical property of a biological fluid sample wherein the sample is treated with a surfactant prior to sample analysis.

BACKGROUND OF THE TECHNOLOGY

A variety of chemical and physical parameters of biological fluids are routinely analyzed in the diagnosis of disease and in routine monitoring of medical conditions.

Many biological fluids must be processed prior to analysis to remove interfering proteins, biomolecules, or bulk properties of the sample. This can present difficulties in obtaining and validating the results obtained from biological sample analysis. Reliability and reproducibility of data is critical. Hence simple sample preparation methods that yield accurate, reliable and reproducible results are highly desirable.

The sample preparation process has a direct im pact on such analyses in terms of accuracy, precision, and quantitation limits. Effective sample preparation is extremely important to the analytical process. Optimally, the sample preparation process is relatively fast, easy, and an inexpensive means to obtain accurate and consistent results when analyzing a chemical or physical parameter of a biological fluid.

Non-invasive sample collection alternatives that reduce or eliminate the skin trauma, pain, infection risk and blood waste associated with traditional blood tests are also preferred.

Salivary diagnostics is an emerging field that relies on saliva as an easily-obtainable biological fluid for detection or diagnosis of various diseases and medical conditions. Unprocessed saliva is a viscous inconsistent fluid with unusual shear properties and which contains a number of proteins. These properties of saliva make it difficult to analyze bulk properties of saliva. Laboratory techniques such as solvent extraction, centrifuge filtration and/or relatively long periods of settling in sealed containers are often used to make saliva more amenable to subsequent analysis.

A noninvasive means to evaluate chemical or physical parameters of biological fluids, such as saliva, that is portable, simple, rapid to use, and which provides accurate, reliable and reproducible results is highly desirable. The present invention addresses this need.

BRIEF SUMMARY

In one aspect, methods for measuring a physical or chemical property of a biological fluid are provided. The methods comprise providing a biological fluid sample; treating the sample with an anionic surfactant, further providing a sensor comprising a hydrogel having a physical or chemical property, wherein the initial value of the physical or chemical property is known and the hydrogel is characterized by a change in the physical or chemical property in response to exposure to an anionic surfactant-treated biological fluid sample; contacting the hydrogel with the anionic surfactant-treated biological fluid sample; evaluating the change in the hydrogel; and correlating the change in the hydrogel with a physical or chemical property of the biological fluid.

Exemplary biological fluids include saliva, whole blood, plasma, serum, lymph, synovial fluid, peritoneal fluid, pleural fluid, urine, sputum, semen, vaginal lavage, bone marrow, cerebrospinal cord fluid and tears.

Exemplary physical properties include absorption at a given wavelength, density, electric conductivity, pH, osmolality, osmolarity, thermal properties, viscosity, dielectric constant, refractive index and light scattering.

Exemplary chemical properties include the concentration of glucose, creatinine, urea, cortisol, total protein, total electrolytes, estrogen, progesterone, testosterone, a cation, e.g., sodium ($Na^+$); calcium ($Ca^{2+}$); potassium ($K^+$), or magnesium ($Mg^{2+}$); an anion, e.g., chloride ($Cl^-$); fluoride (Fl); bromide (Br); sulfate ($SO_4^{2-}$); nitrate ($NO_3^-$); carbonate ($CO_3^{2-}$); and bicarbonate ($HCO_3^-$).

The measured change in a physical or chemical property of the hydrogel is typically a change in volume, a change in optical density, a change in refractive index, a change in AC conductivity or capacitance.

Exemplary hydrogels are cross-linked and have a net negative charge, e.g., a cross-linked hydrogel comprised of an acrylamide moiety, a hydroxyalkyl acrylate or a hydroxyalkyl methacrylate, vinyl ether, or vinyl pyrrolidone which comprises an anionic moiety selected from a carboxylate group, a sulfate group, a sulfonate group and a phosphate group.

Exemplary anionic surfactants are selected from the group consisting of a fatty acid salt, an alkyl or alkyl aryl sulfate, sulfonate or sulfonic acid, a sulfoacetate, an alkyl or alkyl aryl phosphate, phosphate esters, dioctyl sulfosuccinates, alkyldiphenyloxide disulfonate salts, a sulfosuccinate, a lactylate, sodium dodecyl sulfate (SDS) and dodecylbenzene sulfate (DBS).

The final concentration of the anionic surfactant is generally from about 0.01% to about 0.25%; from about 0.02% to about 0.15% and/or the anionic surfactant has a critical micelle concentration in water of less than 1%.

In one preferred embodiment, the anionic surfactant is SDS and the final concentration is from 0.01M to about 0.1M, preferably from 0.03M to about 0.07M, wherein the SDS has less than 1% (w/w) of non surfactant impurities.

In another preferred embodiment, the biological fluid is saliva, the measured physical property is osmolality, the anionic surfactant is SDS and the measurement is based on a change in volume of the hydrogel.

In another aspect, hydrogel sensor systems for measuring a physical or chemical property of a surfactant-treated biological fluid sample are provided. The hydrogel sensor systems typically comprise a cartridge for collecting and treating a biological fluid sample with an anionic surfactant and a means for attaching or transporting the sample to a device comprising a hydrogel sensor effective to measure a physical or chemical property of the biological fluid. The device typically comprises a movable microcantilever sensor having a known resistance corresponding to an initial position of the tip of the microcantilever. The cantilever may be free standing with a hydrogel layer disposed on one side or may comprise a hydrogel secured to a rigid substance and positioned against the microcantilever, wherein the change in a physical property of the hydrogel deflects the microcantilever and a signaling component which creates a detectable signal in response to movement of the microcantilever. In another embodiment the hydrogel sensor system may comprise a hydrogel contacting a pressure sensor or disposed on a reflective surface.

In some embodiments, the sensor is disposable.

BRIEF DESCRIPTION OF THE DRAWINGS

The methods, systems, and devices are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

A. Introduction

Figure 1:
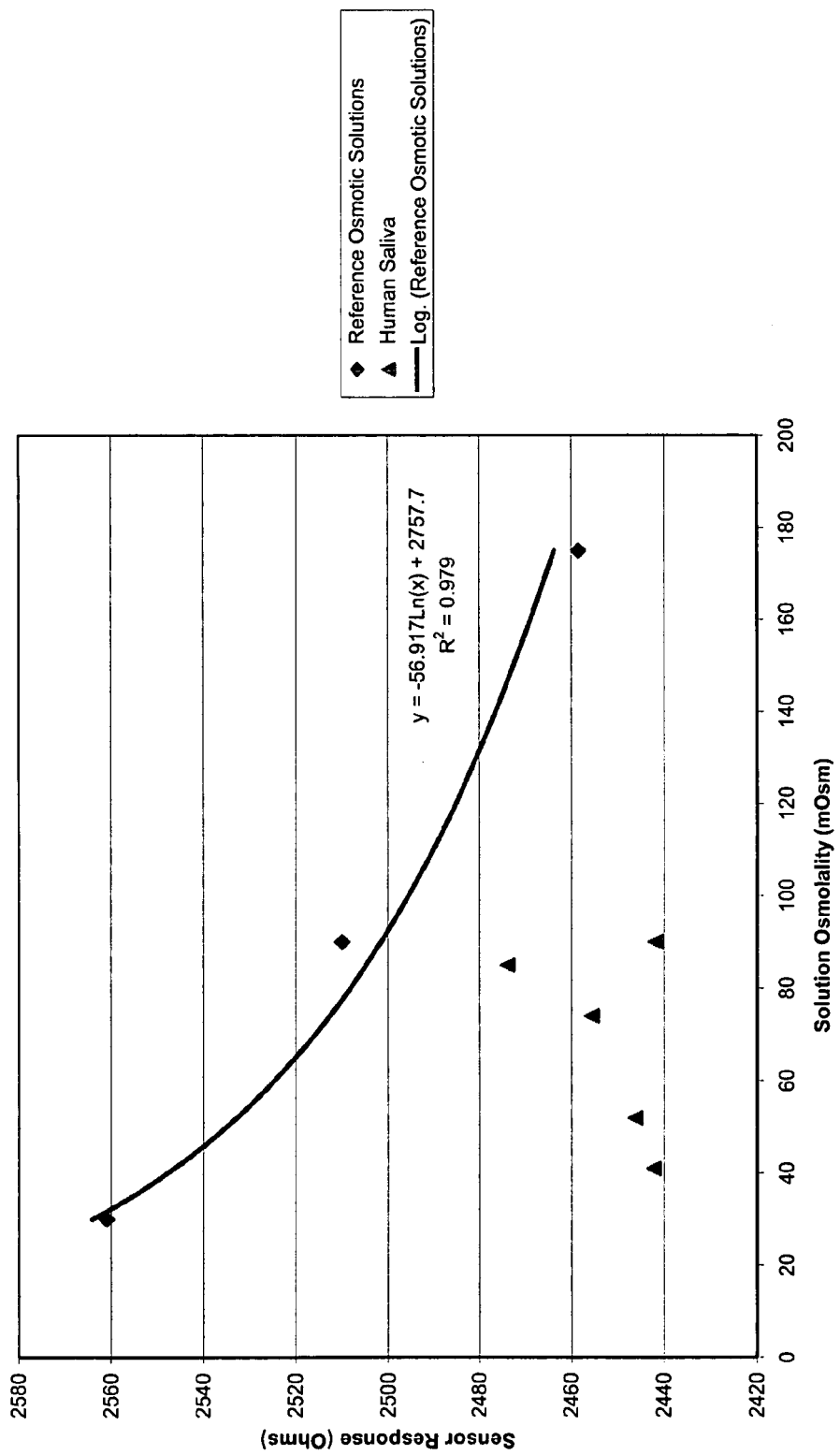
FIG. 1 is a graphic depiction of cantilever resistance (Ohms) versus solution osmolality (mOsm), for reference NaCl solutions and human saliva samples.

Compositions, devices, methods and systems for determining a physical or chemical property of a biological fluid using a device are provided. Methods for treating the biological fluid are provided such that the interference of substances found in the biological fluid with the accuracy of the physical or chemical property determination is minimized or eliminated.

Following treatment, the biological fluid sample is put in contact with a hydrogel which acts as a sensing material on a detecting device. The hydrogel undergoes a physical or chemical change, e.g., volumetric expansion or contraction in response to a physical or chemical property of the biological fluid. The change is correlated with a physical or chemical property of the biological fluid. The change may be qualitative or quantitative. The device records and displays the results of the change, such that a physical or chemical property of the biological fluid is measured.

The following disclosure describes the compositions, methods, systems and kits which constitute the invention. The invention is not limited to the specific, devices, methodology, systems, kits or conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

The publications discussed herein are provided solely for their disclosure prior to the filing date of the present application. Nothing herein is to be construed as an admission that the invention is not entitled to antedate such a disclosure by virtue of prior invention.

B. Definitions

The term "biological fluid" is used herein with reference to a biological fluid taken from a subject selected from the group consisting of saliva, whole blood, plasma, serum, lymph, synovial fluid, peritoneal fluid, pleural fluid, urine, sputum, semen, vaginal lavage, bone marrow, cerebrospinal cord fluid and tears. Frequently the sample will be a "clinical sample" which is a sample derived from a patient.

The term "chemical property" is used herein with reference to a property of a biological fluid that becomes evident during a chemical reaction or the amount of a particular chemical entity in a biological fluid.

The term "MEMS" or "Micro-Electro-Mechanical Systems" provide for the integration of mechanical elements, sensors, actuators, and electronics on a common silicon substrate through microfabrication technology.

The term "physical property" is used herein with reference to any aspect of a biological fluid that can be measured, evaluated or observed without changing the sample.

The term "osmolality" is used herein with reference of the osmoles of solute per kilogram of solvent. An osmole (Osm) is a unit of measurement that defines the number of moles of a chemical compound that contribute to a solution's osmotic pressure. In the laboratory setting, osmolality is commonly measured using an osmometer and the freezing point depression method. One mole (the molecular weight in grams) of any substance dissolved in one kilo of water will cause an osmotic pressure of 17,000 mmHg, a boiling point elevation of 0.52° C., a vapor pressure decrease of 0.3 mmHg and a freezing point depression of −1.86° C. and corresponds to an osmolality of 1000 mOsmols per kilo of water (1000 mOsmols). Using the freezing point depression method, 1 mOsmol will produce a temperature change of only 0.0018° C.

The term "osmolarity" is used herein with reference to the osmoles of solute per liter of solution. Molarity and osmolality are not commonly used in asymmetry because they are temperature dependent; and water changes its volume with temperature.

The terms "phase change" and "phase transition" are used interchangeably herein and include evaporation, melting and freezing of water, the formation of frost and snow, and the sublimation of dry ice which are well-known phenomena, and are examples of five of the six common changes in state: (i) melting of a solid into a liquid; (ii) freezing of a liquid into a solid; (iii) evaporation of a liquid into a gas; (iv) condensation of a gas into a liquid; (v) the vaporization (sublimation) of a solid into a gas; and (vi) the freezing of a vapor into a solid.

The changes are listed in parts in which each process of the pair is the reverse of the other. When the substance has polymorphic solid forms such as a hydrogel, other phase transitions are possible. Such transitions are described in US Patent Publication No. 20070249059 (expressly incorporated by reference herein).

The term "melting point" is used herein with reference to another phase change of interest in polymeric systems. Because polymers are usually statistical mixtures of individual components they typically have broader melting point ranges than pure elements or compounds. Melting points of polymers, including gels, can be measured by calorimetric methods, for example differential scanning calorimetry, or by optical methods or mechanical methods.

The term "microcantilever" is used herein with reference to a device that can act as a physical or chemical sensor by detecting changes in cantilever bending or vibration frequency. Adsorption stress on one side of the cantilever can be used as a means of detecting a physical or chemical property, e.g., the swelling or shrinking of a hydrogel. Depending on the nature of the change in the hydrogel, the deflection can be up or down. The deflection is proportional to the change. Microcantilevers are micro-electromechanical systems (MEMs) that can be micromachined and mass-produced from single crystal silicon wafers or similar material including SU8 resin. Microcantilevers offer high sensitivity and selectivity for a wide variety of biological and chemical sensing.

As used herein the term "piezoresistive" refers to a material having an electrical resistance which decreases in response to compression caused by mechanical pressure applied thereto in the direction of the current path. Such piezoresistive materials can be, for example, resilient cellular polymer foams with conductive coatings covering the walls of the cells, or elastomers containing conductive particles. As a piezoresitive microcantilever deflects, it undergoes a strain that will apply stress to a piezoresistor element, thereby causing a change in resistance that can be measured by electronic means. One advantage of the piezoresistive method is that the readout system can be integrated on a chip.

The term "resistance" refers to the opposition of the material to the flow of electric current along the current path in the material and is measured in ohms. Resistance increases proportionately with the length of the current path and the specific resistance, or "resistivity" of the material, and it varies inversely to the amount of cross sectional area available to the current. The resistivity is a property of the material and may be thought of as a measure of (resistance/length)/area. More particularly, the resistance may be determined in accordance with the following formula:

$$R=(rho*L)/A \qquad (I)$$

where: R=resistance in ohms; rho.=resistivity in ohm-inches; L=length in inches; and A=area in square inches. The current through a circuit varies in proportion to the applied voltage and inversely with the resistance, as provided in Ohm's Law:

$$I=V/R \qquad (II)$$

where I=current in amperes; V=voltage in volts; and R=resistance in ohms.

The term "S.D.S." or "SDS", is used herein with reference to sodium dodecyl sulfate, an anionic surfactant.

The term "S.L.S." or "SLS" is used herein with reference to sodium laurel sulfate, an ionic surfactant.

The term "NP10" (Tergitol® NP-10), is used herein with reference to NP10, a non-ionic surfactant.

The term "DBS" is used herein with reference to dodecylbenzene sulfate, an anionic surfactant.

SURFACTANTS

A surfactant which dissociates in water and produces cations and anions (zwitterions) is considered to be ionic and may be referred to as a cationic, anionic, zwitterionic surfactant, depending upon the nature of the charge on the surfactant. A surfactant which does not dissociate is called a non-ionic surfactant. An anionic surfactant (also called an anionic detergent) is negatively charged, i.e., it has an anionic hydrophilic group.

A surfactant for treating a biological fluid sample prior to measuring a physical or chemical property of the fluid according to the methods described herein may be an anionic surfactant, a cationic surfactant or a nonionic surfactant.

In one preferred approach, the surfactant is an anionic surfactant. Examples of anionic surfactants are selected from the group consisting of a fatty acid salt, an alkyl or alkyl aryl sulfate, sulfonate or sulfonic acid, a sulfoacetate, an alkyl or alkyl aryl phosphate, phosphate esters, dioctyl sulfosuccinates, alkyldiphenyloxide disulfonate salts, a sulfosuccinate, a lactylate, sodium dodecyl sulfate (SDS) and dodecylbenzene sulfate (DBS). One exemplary anionic surfactant is AKYPO RLM 100.

Commercially available surfactants may contain impurities which can be removed using conventional techniques such as, for example, molecular exclusion chromatography in the case of the nonionic surfactants and ion exchange chromatography in the case of the anionic surfactants. In one preferred embodiment, the final concentration of the anionic surfactant is from about 0.01% to about 0.25%; from about 0.02% to about 0.15%.

In a particularly preferred embodiment, the anionic surfactant is from about 0.01M to about 0.1M SDS, preferably from about 0.03M to about 0.07M SDS, wherein the SDS has less than 1% (w/w) of non surfactant impurities.

In another preferred embodiment, the anionic surfactant has a critical micelle concentration in water selected from the group consisting of less than 1%, less than 0.5% and less than 0.1%.

METHODS AND COMPOSITIONS FOR MEASURING A PHYSICAL OR CHEMICAL PROPERTY OF A BIOLOGICAL FLUID.

Provided herein are compositions and methods for measuring a physical or chemical property of a biological fluid collected from a subject. In carrying out the method: (1) a biological fluid is collected from a subject; (2) the biological fluid is treated with a surfactant; (3) a device comprising hydrogel sensor having a known initial physical or chemical characteristic is provided, wherein the hydrogel is characterized by a change in the physical or chemical characteristic in response to a physical or chemical property of the biological fluid; (4) the surfactant-treated biological fluid is placed in contact with the device/hydrogel sensor; (5) a physical or chemical property of the hydrogel sensor is evaluated following exposure to the surfactant-treated biological fluid sample, for example, a change in volume, or a change in an electrical property, e.g., AC conductivity, capacitance or resistance of the hydrogel; and (6) the change in a physical or chemical property of the hydrogel sensor is correlated with a particular physical or chemical property of the biological fluid sample.

Any means of sample collection and anionic surfactant treatment may be used to prepare a biological fluid sample for analysis. The sample collection vessel is typically disposable, contains a predetermined amount of anionic surfactant and is designed for collection of a predetermined sample volume. A sample volume is typically from about 150 to 250 microliters (uLs), but as one of skill in the art will understand, the sample size may vary and can be significantly greater or less than 250 uLs dependent upon the reaction conditions. Prior to carrying out sample analysis, anionic surfactant treatment of a biological fluid sample typically involves thorough mixing of the surfactant with the sample and allowing the mixture to reach equilibrium, such that interfering ionic materials are removed from the sample prior to analysis.

In carrying out the analysis of a biological fluid sample, the sensor comprises a detecting means such as an optical refractometer, an interferometer or one or more electric circuits which can detect a change in a measurable physical property or properties of the hydrogel. In a specific embodiment the volume of the hydrogel is monitored with a microcantilever. A particular physical or chemical property of the sensor may be measured prior to and after the introduction of a biological fluid sample to the sensor and the results compared to detect a change and the degree of change in the physical property or properties of the microcantilever. The change itself can then be associated with, for example the osmolality of a saliva sample. In this exemplary application of the claimed methods, the degree of change corresponds to the degree of microcantilever arm deflection which, in turn, corresponds to the osmolality of the saliva sample.

The device includes a means for detecting a change in a measurable physical or chemical property of the sensor. As will be understood by those of skill in the art, resistance is one example of a measurable physical property used to detect a change in the microcantilever. Other examples include, but are not limited to optical transmittance (optical density), refractive index and AC conductivity, which vary in response to chemical or physical changes of the hydrogel.

CHEMICAL AND PHYSICAL PROPERTIES OF A BIOLOGICAL FLUID

The methods and devices described herein find utility in measurement of any chemical or physical property of a biological fluid that may be determined using a sensor comprising a hydrogel.

Exemplary chemical properties are selected from the group consisting of the concentration of a particular component such as glucose, creatinine, urea, cortisol, total protein, total electrolytes, total estrogen, total progesterone total testosterone, a cation, e.g., sodium ($Na^+$); calcium ($Ca^{2+}$); potassium ($K^+$), or magnesium ($Mg^{2+}$); an anion, e.g., chloride ($Cl^-$); fluoride (Fl); bromide (Br); sulfate ($SO_4^{2-}$); nitrate ($NO_3^-$); carbonate ($CO_3^{2-}$); bicarbonate ($HCO_3^-$); or a known biomarker.

Exemplary physical properties are selected from the group consisting of absorption at a given wavelength, density, electric conductivity, pH, osmolality, osmolarity, thermal transfer, viscosity, dielectric constant, refractive index or light scattering.

SALIVA

Saliva is an excellent biological fluid for analysis. It is easily collected using noninvasive techniques and samples can readily be collected at multiple time points.

Analyzing saliva is similar to analyzing blood serum or plasma, due to its protein content and other potential contaminants.

While not wishing to be bound by theory, there are a number of proteins in saliva, e.g., mucin, which can interfere with analysis of biological fluids. When saliva mimic solutions or saliva analogues are formulated to contain mucin, the mucin interferes with hydrogel sensor behavior, suggesting that mucin may interfere with accurate analysis of saliva samples. Mucins are a family of heavily glycosylated proteins secreted by mucosal surfaces and mucin is largely responsible for the viscosity and "stringiness" of human saliva. Mucins are relatively abundant, but in widely varying concentration in human saliva.

In preparing saliva samples for analysis, it is necessary to process samples such that stable readings and accurate and reproducible results are obtained. As described in the examples provided below, the treatment of biological fluid samples such as saliva with an anionic surfactant was effective to yield stable and consistent results using the hydrogel sensors described herein.

A hydrogel sensor for use in a device for measuring saliva osmolality typically comprises a hydrogel responsive to a change in osmolality in the range of 50-250 mOsm.

DEVICES FOR MEASURING PHYSICAL AND CHEMICAL PROPERTIES OF A BIOLOGICAL FLUID

The claimed methods for evaluating a chemical or physical property of a surfactant-treated biological fluid are typically accomplished using a device which comprises a highly sensitive and selective sensor. In one embodiment, the device is comprised of a sensor material secured into a fixed position on a substrate, a deformable arm and a signaling component which creates a detectable signal in response to movement of the arm. The sensitivity of the device is enhanced by using a sensor material, e.g., a hydrogel, which undergoes a dramatic change in volume such as a phase change in response to a target molecule of interest. A change in volume of the sensor material takes place in response to the presence of a particular chemical entity, pH, osmolality, temperature change or other variation in the environment of the hydrogel which moves the arm causing the signaling component (e.g. a piezoresistor) to create a detectable signal (e.g. change in resistance) thereby indicating the presence/amount of the chemical or osmoles in the surfactant-treated biological fluid.

The methods and devices described herein provide a means for evaluating a chemical or physical property of a surfactant-treated biological fluid by contacting the surfactant-treated biological fluid with a hydrogel sensor. In one embodiment, located adjacent to and in contact with the hydrogel sensor is a deflectable arm of a microcantilever. In another embodiment, in the presence of a particular chemical of interest in the surfactant-treated biological fluid sample, the hydrogel sensor undergoes a change in volume wherein expansion causes the deflectable microcantilever arm to deflect upward. In yet another embodiment, the hydrogel undergoes a physical or chemical change other than a volumetric change (i.e. other than swelling or shrinking). Examples of which include changes in AC conductivity, capacitance, ionic mobility, resistance, optical transmittance, fluorescence, refractive index or a viscoelastic property of the hydrogel.

Alternatively, in another embodiment, in response to a particular physical property of the surfactant-treated biological fluid sample, the hydrogel undergoes a volumetric contraction resulting in a downward displacement of the deflectable arm of the microcantilever. Devices for evaluating a chemical or physical property of a surfactant-treated biological fluid are described for example in United States Patent Publication No. 20070249059, expressly incorporated by reference herein.

In one embodiment, the hydrogel is disposed on one side of a microcantilever. In another embodiment the microcantilever is formed on a substrate separate from the surface including the sensing material. Conventional semiconductor processing technology may be used to form the microcantilever. Various configurations and orientations of the microcantilever may be used. The microcantilever includes an overhang portion which extends over the edge of the microcantilever substrate and allows for the substrate and the surface containing the sensing material to be positioned in close proximity to one another such that the deflectable arm of the microcantilever is situated above and in contact with the sensing material. A micromanipulator may be used to position and align the components. The deflectable arm of the microcantilever includes at least one measurable physical property which changes when the deflectable arm deflects in response to a volumetric change of the hydrogel sensor. The devices described herein also provide a detecting means in the form of various electric circuits which detect a change in position of the deflectable arm.

The microcantilever may be calibrated to correlate a measured change in the surfactant-treated biological fluid sample with a chemical or physical property of the biological fluid. In the case where the chemical or physical property of the biological fluid is not detectable, e.g., a specific chemical analyte is not present, the microcantilever will not deflect and therefore the measurements taken before and after the introduction of the surfactant-treated biological fluid sample will be substantially the same.

One preferred sensor is a micro-electro-mechanical systems (MEMS) device comprising a piezoresistive microcantilever 20 μM wide, 300 μM long and 3 μM thick and surrounding die, and wire-bonded connector and female pin block. Nominal resistance across the cantilever is 2.2 kOhms and increases approximately 1 Ohm for each micron the cantilever tip is deflected from neutral. In this embodiment, a hydrogel is secured to a rigid substrate and positioned against the microcantilever such that swelling of the hydrogel deflects the micro-cantilever.

The device further comprises a signaling component which undergoes a change such as a change in resistance, resonant frequency, electrical output, or capacitance in response to very small movements of the microcantilever arm, or in the case of a resonator, to the rheological properties of the materials it is contact with.

HYDROGELS

During the detection process, the sensor material undergoes a change in volume whereby a hydrogel sheet of, for example a thickness of about 5, 10, 20, 50 or 100 microns expands or contracts 0.5% or more, 1% or more, 5% or more, or 10% or more and is detected by the arm capable of detecting movement of in a range of 1 to 1,000 angstroms or more which may include a phase change.

Hydrogels are three dimensional networks of hydrophilic polymers which are crosslinked to form water-swellable but water insoluble structures. The term hydrogel is to be applied to hydrophilic polymers in a dry state (xerogel) as well as in a wet state. These hydrogels can be crosslinked in a number of ways, as described for example in United States Patent Publication No. 20070249059, expressly incorporated by reference herein. Alternatively, hydrogels may be crosslinked with ionic species or by incorporation of self associating monomers resulting in physical crosslinking or may be effectively be rendered insoluble by incorporation into an interpenetrating network.

Exemplary hydrogel chemical sensor materials include partially hydrolyzed poly(vinyl acetate) (PVA), poly(ethylene vinyl acetate) (PEVA), modified PEVA, poly(4-vinylphenol), poly(styrene-co-allyl alcohol), poly(N-vinylpyrrolidone), poly(alkylethers) including poly(ethylene oxide) and poly(ethylene oxide) co-polymers poly(vinylethers), poly (hydroxyalkylacrylates) or methacrylates or acrylamides including hydroxyethylacrylate, and hydroxypropyl acrylate, substituted or unsubstituted acrylamide or methacrylamide, including n,n-dimethylacrylamide, n-isopropylamide and other known hydrogels.

On example of the basic construction of a fully functional sensor involves determining the neutral resistance of the sensor, then affixing a substrate and hydrogel to the die such that the hydrogel deflects the cantilever as it swelled. In this exemplary approach, hydrogel polymers may be drawn and cured as fibers with approximately 25 μM diameter, cut to approximately 200 μM long sections, and cured on a silane treated silicon wafer fragment. This fragment is then affixed against the sensor die with epoxy to create a "hydrogel fiber sensor".

Alternatively, the surface of silane treated silicon wafers may be coated with a hydrogel polymer solution in an even continuous layer; achieved by way of natural surface tension of poured polymer, spin coating, or surface repulsion from the low-surface-energy side of Mylar film placed on top of the wet hydrogel polymer. Hydrogel sensors can also readily be prepared using photolithographic methods.

MODIFICATION OF HYDROGELS TO IMPROVE SENSOR RESPONSE/TEMPERATURE INSENSITIVE HYDROGELS

Environmentally sensitive hydrogels are well know in the art. Such hydrogels can be used as sensors for temperature, pH and salt concentration. Examples of environmentally responsive hydrogels include poly n-isopropylacrylamide, polydiethylacrylamide and poly hydroxyproply acrylamide.

It has been shown that these kinds of polymers can undergo some kind of a "phase transition" wherein they abruptly swell or deswell in response to a small change in their environment over a narrow range. However, in making a practical sensor it has been found that the selectivity of environmentally sensitive hydrogels is poor, in particular the swelling of such hydrogels in response to pH, salt concentration or chemical concentration have a strong temperature dependence. Therefore to be useful as a chemical, pH or salt sensor, the measurements must either be made at a carefully defined and controlled temperature or it is necessary to develop complex temperature correction factors. In many cases, due to the essentially complete collapse of a hydrogel at a specific temperature, it is not possible to use them above that critical temperature. (See, e.g., publicly available information on "environmentally responsive" or "smart" hydrogels).

It is also known that incorporation of carboxylic acid groups into hydrogels can increase their sensitivity to pH and salt concentration. Unfortunately, addition of carboxylic acid groups typically also increases their sensitivity to temperature.

The inventors have discovered that environmentally responsive, but temperature insensitive hydrogels can be prepared by selective incorporation of low levels of a weakly acidic or basic group which is ionized and neutralized with a water soluble counter ion. This has been achieved and has significant utility in making a wide range of hydrogel based sensors useful for example in determinations of osmolality, sodium and potassium.

In one embodiment a sensor is prepared comprising a hydrogel with at least a first monomer and a second monomer wherein the first monomer gives rise to a normally temperature responsive hydrogel. The second monomer has at least one weak acidic moiety which is present in the anionic form and a charge balancing ion selected from a monovalent metal cation, an ammonium cation, a sulphonium cation and a phosphonium cation. Preferred monovalent metal cations include $Li^+$, $Na^+$, $K^+$, $Cs^+$, $R^+$ and $Fr^+$. Preferably, the first monomer comprises from about 20% to about 99% of the hydrogel and the carboxylic acid bearing monomer comprises from about 0.5% to about 10% of the hydrogel. The first monomer may be a single chemical species or a mixture of one or more monomers. Optionally, additional monomers may be present, provided they do not render the hydrogel non-responsive to the analyte being detected.

In another embodiment, a sensor is prepared comprising a hydrogel with at least a first monomer and a second monomer wherein the first monomer gives rise to a normally temperature responsive hydrogel. The second monomer has at least one weakly basic moiety which is present in the cation form and a charge balancing monovalent anion, which is normally water soluble. Exemplary weakly basic moieties include primary, secondary, tertiary amines and quaternary ammonium compounds, phosphines and phosphonium compounds. Preferably, the first monomer comprises from about 20% to about 99% of the hydrogel and the basic monomer comprises from about 0.5% to about 10% of the hydrogel. The first monomer may be a single chemical species or a mixture of one or more monomers. Optionally, additional monomers may be present, provided they do not render the hydrogel non-responsive to the analyte being detected.

In a preferred approach, the first monomer is selected from an alkyl or dialkly acrylamide or methacrylamide, a hydroxyl alkyl acrylate or methacrylate, methyl-vinyl ether, ethyl vinyl ether, n-vinyl pyrollidone, ethylene oxide, propylene oxide, an amide or substituted urea. In another preferred approach, the weakly acidic monomer is selected from acrylic acid, methacrylic acid, carboxy ethyl acrylate, itaconic acid, carboxy styrene, undecylenic acid, and vinyl phosphoric acid. Preferably the weakly acidic or basic monomer comprises from about 0.5% to about 10% of the dry hydrogel weight.

An exemplary modified environmentally responsive hydrogel and characterization thereof is described in Example 3.

UTILITY

In general, biological fluids must be processed prior to analysis to remove interfering proteins or other biomolecules. The processing step can present difficulties in obtaining accurate and consistent results in analysis of biological samples. Given that reliability and reproducibility of data is critical, simple and effective sample preparation methods that reduce data error are highly desirable.

A noninvasive means to evaluate chemical or physical parameters of biological fluids that is portable, simple and rapid to use, and which provides accurate analytical results is also desirable. Accordingly, there is utility in the claimed devices, methods and systems for analyzing a physical or chemical property of a biological fluid sample using a handheld device comprising a microcantilever-based sensor system. The present invention addresses this need.

The ocular surface requires a complete tear film to maintain health and function. Adequate production, retention, and balanced elimination of tears is necessary for this process. Any imbalance of these components can lead to the condition of dry eye. A single biophysical measurement that captures the balance of inputs and outputs from the tear film dynamics is tear osmolality. It has been suggested that tear hyperosmolality is the primary cause of discomfort, ocular surface damage, and inflammation in dry eye. Hyperosmolality can result from either a decrease in tear secretion or an increase in tear evaporation, the two pathways that produce ocular dryness. Hence, hyperosmolality is believed to be a feature common to all cases of dry eye disease.

A need exists to rapidly and accurately measure properties of tear film, including osmolality. Measurement of tear film osmolality is therefore a convenient and non invasive diagnostic assay.

A serum or blood osmolality test measures the amount of chemicals dissolved in the liquid part of the blood. Chemicals that affect serum osmolality include sodium, chloride, bicarbonate, proteins, and sugar (glucose). A serum osmolality test is done on a blood sample taken from a vein or finger stick. Serum osmolality is measured to: (1) check the balance between the water and the chemicals dissolved in blood; (2) determine if severe dehydration or overhydration is occurring; (3) evaluate antidiuretic hormone (ADH) production by the hypothalamus; (4) determine the cause of seizures or coma, which may be caused by an imbalance between water and electrolytes in the body; (5) determine if a person has swallowed certain poisons. The normal values in serum are 280 to 295 mOsm/L or about 280 to 303 milliosmoles per kilogram (mOsm/kg).

A higher-than-normal serum or blood osmolality level may indicate: (a) dehydration; (b) diabetes insipidus; (c) hyperglycemia; (d) hypernatremia; (e) consumption of methanol; (f) consumption of ethylene glycol; (e) renal tubular necrosis; (f) stroke or head trauma resulting in deficient ADH secretion (cranial diabetes insipidus); of (g) uremia.

A lower-than-normal osmolality level may indicate: (a) excess fluid intake; (b) hyponatremia; (c) overhydration; (d) paraneoplastic syndromes associated with lung cancer; or (e) syndrome of inappropriate ADH secretion.

Osmolality of whole blood and serum are commonly measured using a freezing point or vapor pressure osmometer. The claimed sensors, methods and systems may be used to effectively measure the osmolality of whole blood.

The invention is described by reference to the following examples, which are offered by way of illustration and are not intended to limit the invention in any manner. Standard techniques well known in the art or the techniques specifically described below are utilized. Therefore, the description and examples should not be construed as limiting the scope of the invention, which is delineated by the appended description of exemplary embodiments.

EXAMPLES

MATERIALS AND METHODS

A. Preparation of Sensing Hydrogels.

An osmotic responsive hydrogel precursor was prepared by polymerizing a mixture of hydroxypropyl acrylate, acrylamide and acrylic acid in the ratio of 85:15:1.

The polymerization was carried out in a 70:30 w/w mixture of water and dimethyl formamide utilizing azobisisobutylnitrile (Aldrich Chemical) as initiator. The resulting polymer was utilized as is or purified by washing with hot water. One type of sensor material was prepared by combining the hydrogel precursor with a crosslinking agent and casting a film on a substrate or drawing fibers and subsequently drying and curing the material. Examples of suitable curing agents include aminoplast resin such as Cymel 327 (Cytec), polyazyridines (Cytec), multivalent metal ions such as zinc or zirconium, multifunctional isocyanates, multifunctional aziridines such as CX-100 (DSM) or a wide range of other commercially available reactive curing agents. Alternatively, a hydrogel was formed in place by polymerizing a mixture of hydrogel precursor monomers including a minor amount of a multifunctional monomer, for example ethyleneglycol diacrylate, hexanediol diacrylatge, or other multifunctional materials (for example, the material provided by Cytec under the trade name Ebercryl or by Sartomer). A convenient method of producing a sensor relies on use of a photomask and ultraviolet light to selectively crosslink or polymerize precursor materials to produce hydrogels of a specific thickness, shape and size.

The preparation of hydrogel based sensors is described in a number of publications including US Patent Publication No. 20050164299; Trinh et al, Electronics System Integration Technology Conference, September 2006, Volume 2: 1061-1070; Sorber et al., Anal Chem. 2008 Apr. 15; 80(8):2957-62. Epub 2008 Feb. 28; and Richter et al., "Review on Hydrogel-based pH Sensors and Microsensors" in *Sensors*, 2008, 8: 561-581 (see pages 566-571); each of which is expressly incorporated by reference herein.

Sensors for measuring osmolality were constructed utilizing peizoresistive microcantilevers (Cantimer, Inc., Menlo Park Calif.). The cantilevers utilized have approximate dimensions of 200 microns long×20 microns wide by 3 microns thick. A second silicon substrate pattern was coated via UV lithography with hydroxypropyl acrylate based hydrogel discs of approximately 25 microns thick and 100 micron diameter. The coated substrate was singulated and bonded to the cantilever substrate using a photocurable epoxy resin such that about ¼ of the cantilever was in contact or directly above the hydrogel. Sensors were equilibrated in 50 mOsmol sodium chloride solution adjusted to pH 9 and then rinsed in deionized water prior to use. Baseline cantilever resistance for each sensor was measured and calibration curves prepared by exposing the sensor to a range of buffered salt solutions.

B. Measuring Solution Osmolality

Solution osmolality measurements were carried out by filling a 1.7 mL VWR microcentrifuge tube with 1 mL of analyte, and placing it in a flow-through temperature controlled block, hooked to a Fischer Scientific 9110 recirculating chiller filled with distilled water. Unless otherwise stated, the recirculating chiller was set to maintain a temperature of 25° C. The sensor was connected to a wiring harness, which descended into a microcentrifuge tube seated in a temperature control block. Foam insulation placed around the block provided for additional thermal control.

A hydrogel sensor was placed in a fluid sample such that the entire die was submerged. The resistance of the microcantilever was tracked on an Agilent 34970A data acquisition system with a sampling frequency of 1 Hz to $\frac{1}{10}$ Hz. When the resistance changes of the cantilever were stabilized, the value was recorded and compared to a curve unique to that sensor derived from resistances produced in standard NaCl solutions of known osmolality (measured by a Fiske 110 freezing point depression osmometer) to determine the sample solution's osmolality.

C. Measuring Salivary Osmolality

Saliva samples obtained from volunteers were collected via expectoration into glass vials. Volunteers were instructed to refrain from eating or drinking for at least 30 minutes prior to providing a sample. The initial sample was pipetted into 0.5 mL aliquots in microcentrifuge tubes for measurement as described in Section A, above. No filtration, purification or centrifugation was preformed on the saliva samples prior to analysis. Saliva was collected unstimulated except for the act of expectoration and the psychological anticipation of providing a sample.

Example 1

MEASUREMENT OF OSMOLALITY OF UNTREATED SALIVA SAMPLES AS COMPARED TO STANDARD METHODS OF SAMPLE PREPARATION

A. Measurement of Osmolality of Untreated Saliva Samples.

Initial attempts to obtain osmolality data from saliva using a hydrogel sensor was met with unstable osmolality readings and inconsistent results. Attempts to determine the osmolality of human saliva, led to sensor measurements which were slow, inaccurate, not reproducible, and elevated when compared to sensor measurements of saline solutions of similar osmolality (as determined by freezing point depression osmometry).

More specifically, when a hydrogel sensor was placed directly into an unprocessed saliva sample, the response of the sensor would take 15 minutes to over an hour to achieve a rate of change of cantilever resistance less than 0.1 Ohm/minute. Repeat measurements of identical saliva samples yielded inconsistent results, particularly if separated by different samples.

The cantilever resistance is correlated with the swelling state of the hydrogel. The imputed osmolality measurements were elevated. In other words, the swelling of the hydrogel in a saliva sample was significantly less than the swelling experienced by the hydrogel in a saline solution of the same osmolality as the saliva sample in question (FIG. 1).

B. Measurement of Osmolality of Saliva Samples Treated with Activated Carbon

Activated carbon treatment followed by filtration was evaluated as a possible way to remove interfering materials from saliva to improve the stability and accuracy of response of a hydrogel sensor in measurement of the osmolality of saliva samples. Saliva samples were treated by storage in a sealed vial with activated carbon for 15 minutes with 0.1 g/ml or 0.3 g/ml of activated carbon, followed by pipetting into microcentrifuge tubes for osmolality determination with a hydrogel sensor and by way of freezing point depression osmometry.

Figure 2:
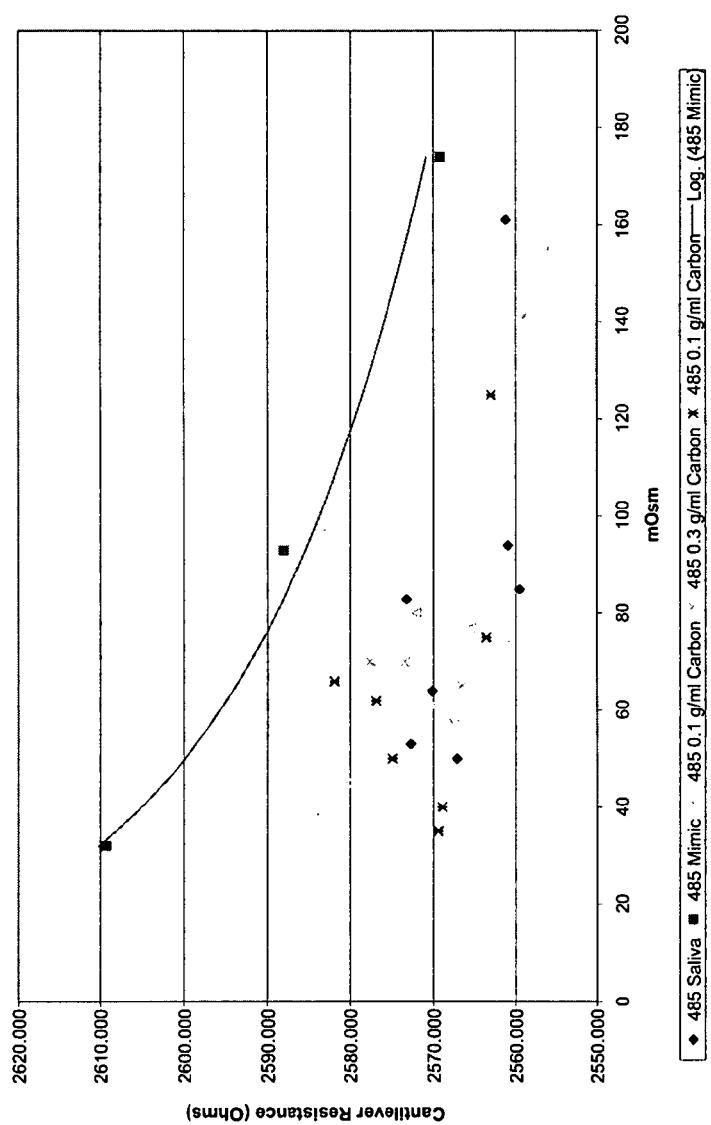
FIG. 2 is a graphic depiction of cantilever resistance (Ohms; sensor 485) versus solution osmolality (mOsm), for a human saliva sample (485 saliva); a reference NaCl solution (484 mimic), and saliva samples treated with activated carbon.

The results shown in FIG. 2 from sensor #485, indicate that activated carbon treatment did not improve the results when osmolality was evaluated using a hydrogel sensor. FIG. 2 is a graphic depiction of cantilever resistance (Ohms; sensor 485) versus solution osmolality (mOsm), for a human saliva sample (485 saliva); a reference NaCl solution (484 mimic), and saliva samples treated with: 0.1 g/ml activated carbon (485 0.1 g/ml Carbon); 0.3 g/ml activated carbon (485 0.3 g/ml Carbon); 0.1 g/ml activated carbon (485 0.1 g/ml Carbon).

Figure 3:
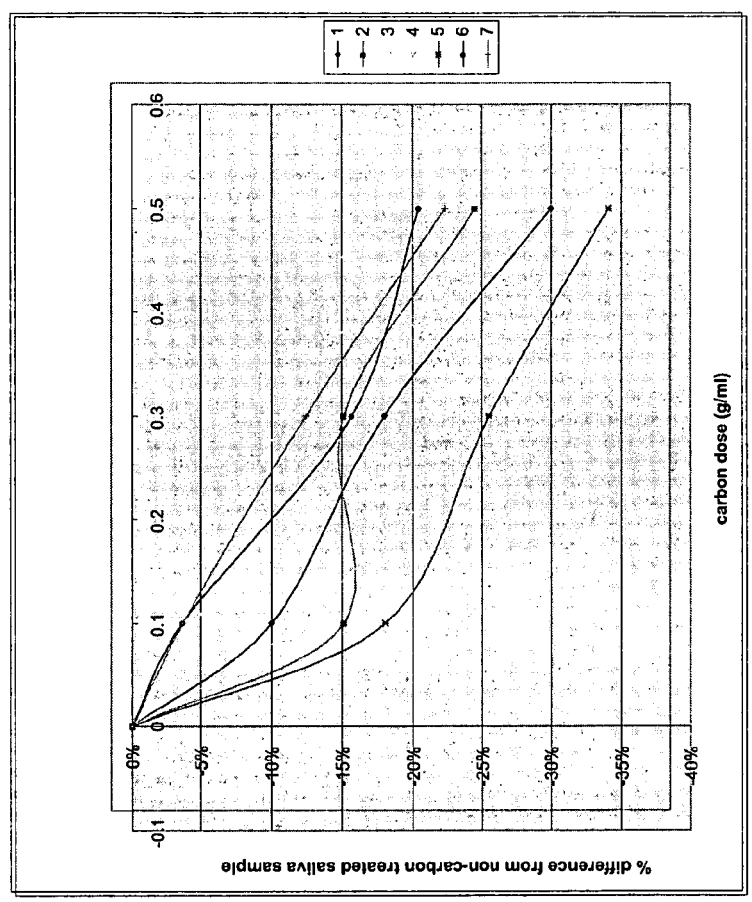
FIG. 3 is a graphic depiction of the effect of activated carbon treatment (0-0.6 g/ml) on individual saliva samples from seven volunteers.

Following activated carbon treatment, the osmolality of the saliva sample decreased, as shown in FIG. 3, which shows the difference in osmolality between original and post-activated carbon-treated saliva samples from 7 volunteers. FIG. 3 provides a graphic depiction of the effect of activated carbon treatment (0-0.6 g/ml) on individual saliva samples from seven volunteers, reported as the percent (%) difference from non-carbon treated saliva samples. The reduction in osmolality for saliva from each of the 7 subjects indicates the carbon successfully adsorbed some solutes from saliva, but did not solve the problem of unstable osmolality readings and inconsistent The reduction in osmolality indicates the carbon successfully adsorbed some solutes from saliva, but did not solve the problem of unstable osmolality readings and inconsistent results, which was observed with untreated saliva samples.

C. Measurement of Osmolality of Model Samples Treated by Centrifugation

Using mucin as a model for an interfering saliva component, mucin containing saliva mimic solutions were prepared and processed using centrifuge filtration with 0.45 uM and 100 k MWCO (molecular weight cut-off) centrifuge filters. 100 k MWCO filtration was found to modestly improve the response of a hydrogel sensor in mucin solutions, but resulted in a poor yield and impractical handling requirements for a portable device.

D. Measurement of Osmolality of Saliva Samples Treated by Flocculent Addition

A generic "pool cleaner" type cationic flocculent was added to saliva samples in an attempt to precipitate larger biomolecules from the sample prior to measurement of osmolality using a hydrogel sensor. Flocculent was added at a concentration of 2 uL per 1 mL of saliva, and mixed. The samples were spun down in a microcentrifuge (Eppendorf 5415C at top speed) for 10 minutes. The supernatant was pipetted out and sampled using a hydrogel sensor and freezing point depression osmometry, as described above.

Example 2

MEASUREMENT OF OSMOLALITY OF SALIVA SAMPLES TREATED BY DOWFAX 2A1, TRITON GR-5M, DOWFAX C10L, TRITON H-55, AND WITCONATE P-1059 SURFACTANTS

A set of surfactants were tested in mimic solutions for compatibility with a hydrogel sensor to determine if they are effective to cause the hydrogel sensor to accurately and consistently determine the osmolality of saliva as compared to that of standard NaCl solutions of known osmolality. Dowfax 2A1, Triton GR-5M, Dowfax C10L, Triton H-55, and Witconate P-1059 surfactants were added to separate saliva samples in amounts ranging from 1%-5% and the osmolality was measured using a hydrogel sensor and freezing point depression osmometry, as described above. As shown in Table 1, one of the surfactants tested was effective to result in an accurate and consistent determination of the osmolality of saliva using a hydrogel sensor as compared to standard osmometry, when used to treat the saliva sample at a practical concentration. In some cases, the amount of surfactant (and effective concentration) required to result in an accurate and consistent determination of saliva osmolality was so high that the actual osmolar value of the combined solution was significantly different than the saliva sample.

TABLE 1

Effect of Various Surfactants on Saliva Osmolality

| Saliva Treatment Concentration | Saliva FPO (Freezing Point Osmolality) | Measured Osmolality (hydrogel sensor) | Difference |
|---|---|---|---|
| Saliva/0.0% DOWFAX 2A1 | 102 | 200 | 98 |
| Saliva/1.0% DOWFAX 2A1 | 131 | 177 | 46 |
| Saliva/5.0% DOWFAX 2A1 | 255 | 270 | 15 |
| Saliva/0.0% SDBS | 93 | 190 | 97 |
| Saliva/0.2% SDBS | 95 | 135 | 40 |
| Saliva/1.0% SDBS | 96 | 112 | 16 |
| Saliva/0.01M NP-10 | 79 | 115 | 36 |
| Saliva/1.00% DOWFAX C10L | 130 | 140 | 10 |
| Saliva/5.00% DOWFAX C10L | 184 | 200 | 16 |
| Saliva/1.00% GR-5M | 162 | 130 | −32 |

Figure 4:
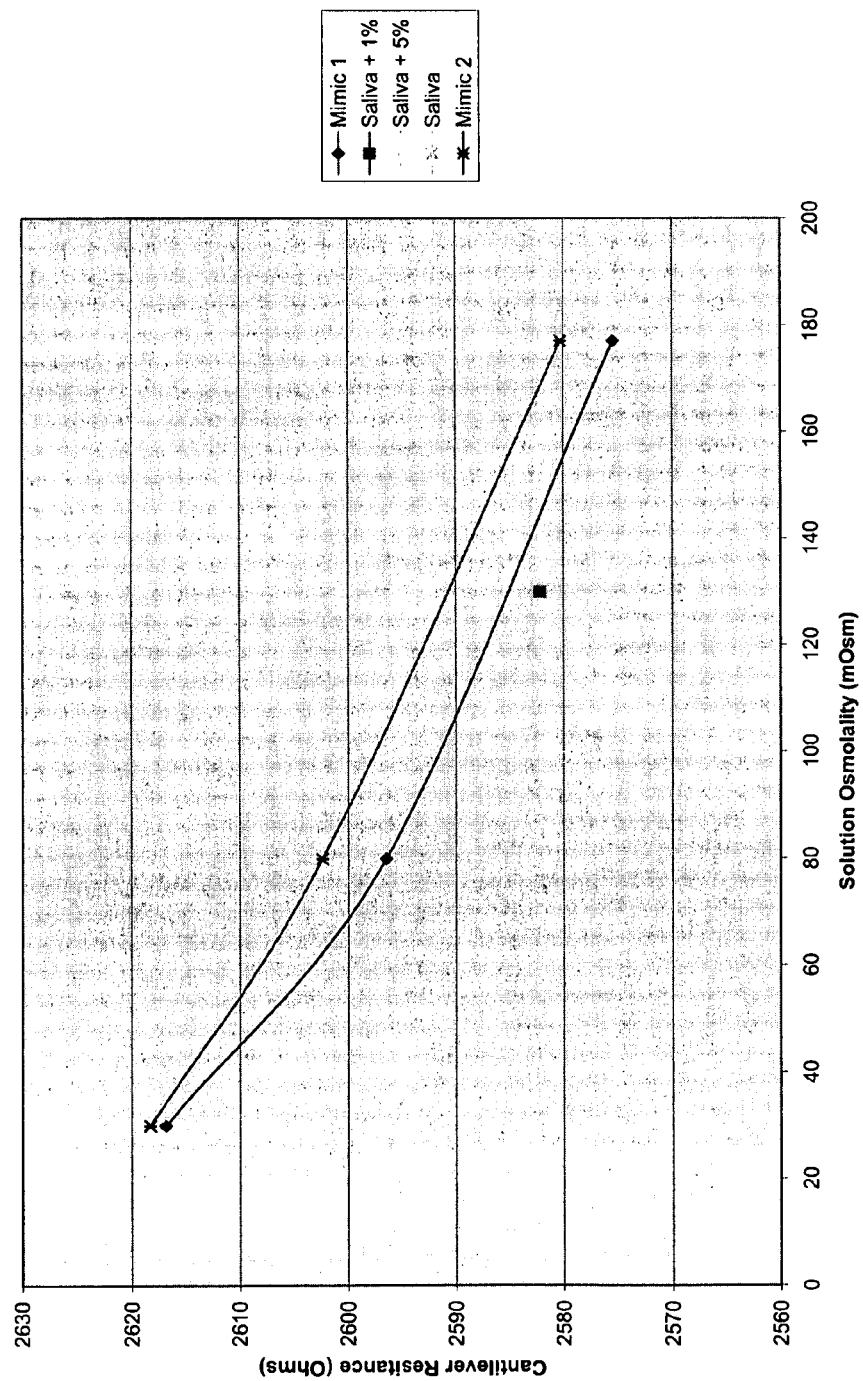
FIG. 4 is a graphic depiction of cantilever resistance (Ohms) versus solution osmolality (mOsm) for 2 NaCl solutions, untreated and Dowfax C10L-treated human saliva samples.

FIG. 4 is a graphic depiction of cantilever resistance (Ohms) versus solution osmolality (mOsm) for 2 NaCl solutions (Mimic 1 and Mimic 2), untreated human saliva (Saliva) and human saliva samples treated with 1% Dowfax C10L (Saliva+1%) or 5% Dowfax C10L (Saliva+5%). The results indicate that Dowfax C10L treatment resulted in close to a tripling of the osmolar concentration of the mixed sample at a concentration of 5%, while not correcting the sensor response.

Figure 5:
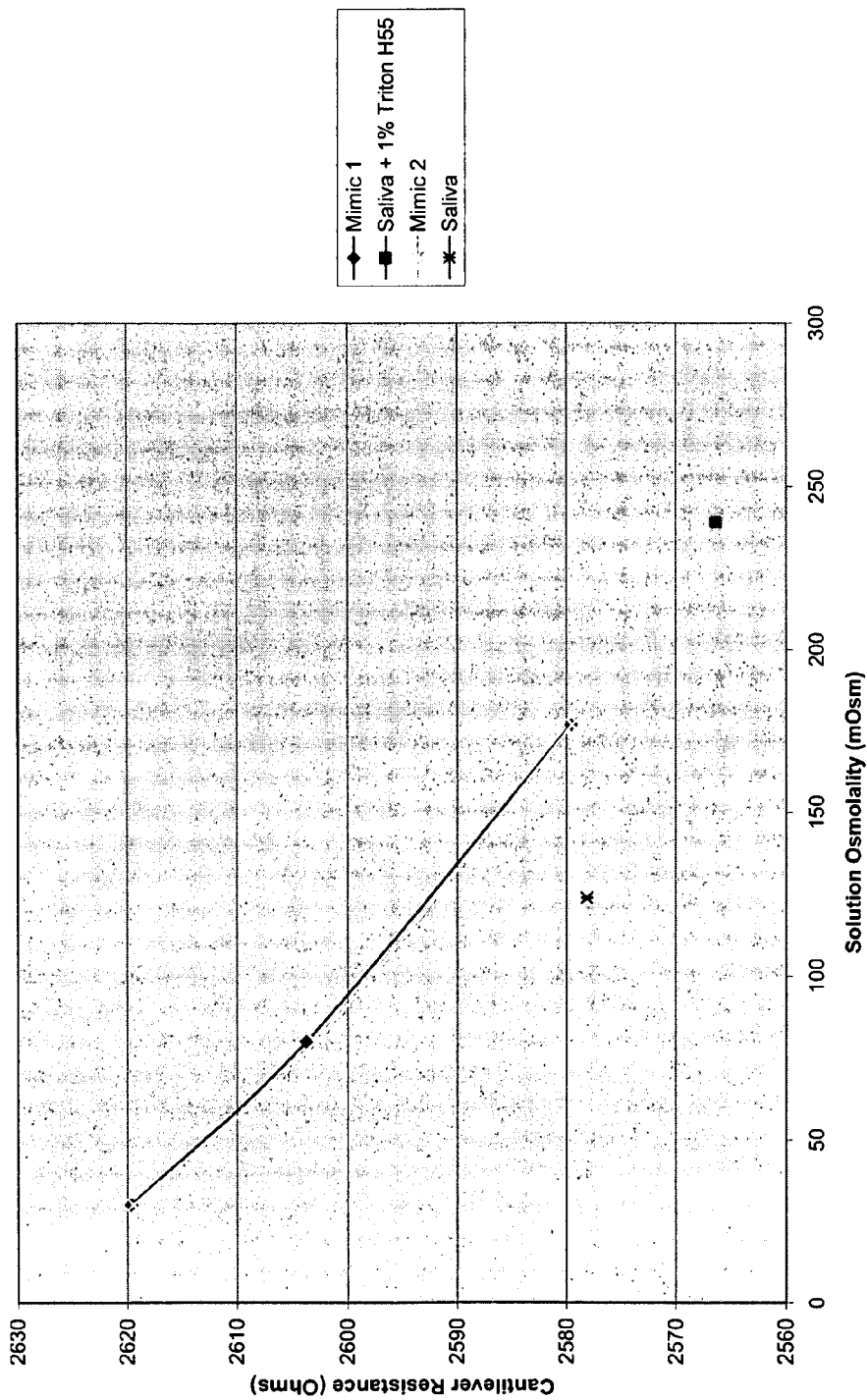
FIG. 5 is a graphic depiction of cantilever resistance (Ohms) versus solution osmolality (mOsm) for 2 NaCl solutions, untreated and a Triton H55-treated human saliva sample.

FIG. 5 provides a graphic depiction of cantilever resistance (Ohms) versus solution osmolality (mOsm) for 2 NaCl solutions (Mimic 1 and Mimic 2), untreated human saliva (Saliva) and Triton H55-treated human saliva (Saliva+1% Triton H55). The results indicate that Triton H55 treatment resulted in a doubling of the osmotic value of the sample when used at a concentration of 1%.

Figure 6:
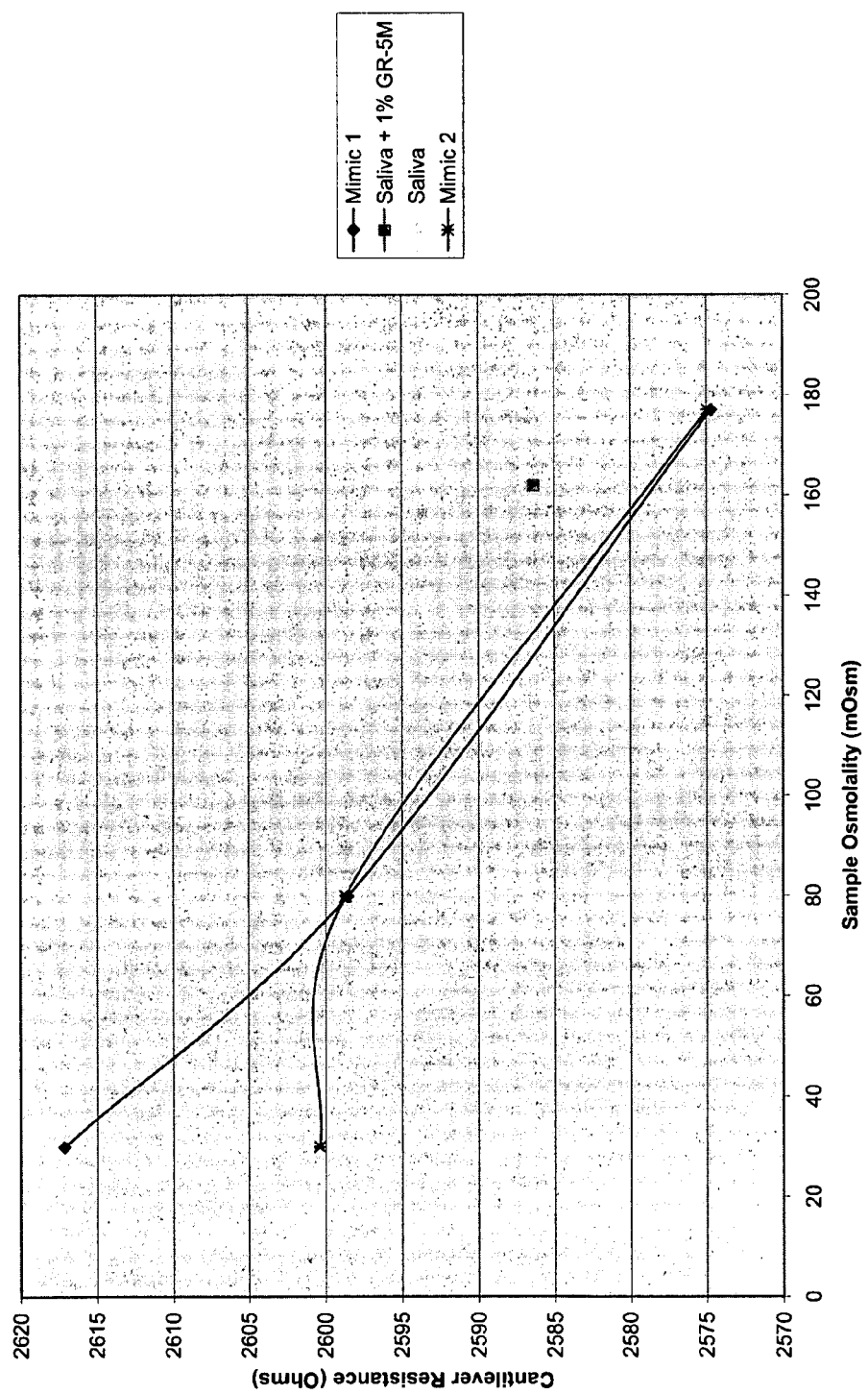
FIG. 6 is a graphic depiction of cantilever resistance (Ohms) versus solution osmolality (mOsm) for 2 NaCl solutions, untreated human saliva (saliva) and human saliva samples treated with 1% Triton GR-5M.

FIG. 6 provides a graphic depiction of cantilever resistance (Ohms) versus solution osmolality (mOsm) for 2 NaCl solutions (Mimic 1 and Mimic 2), untreated human saliva (saliva) and human saliva samples treated with 1% Triton GR-5M (Saliva+1% GR-5M). The results indicate that Triton GR-5M treatment resulted in close to a doubling of the osmotic value of the sample when used at a concentration of 1%.

Figure 7:
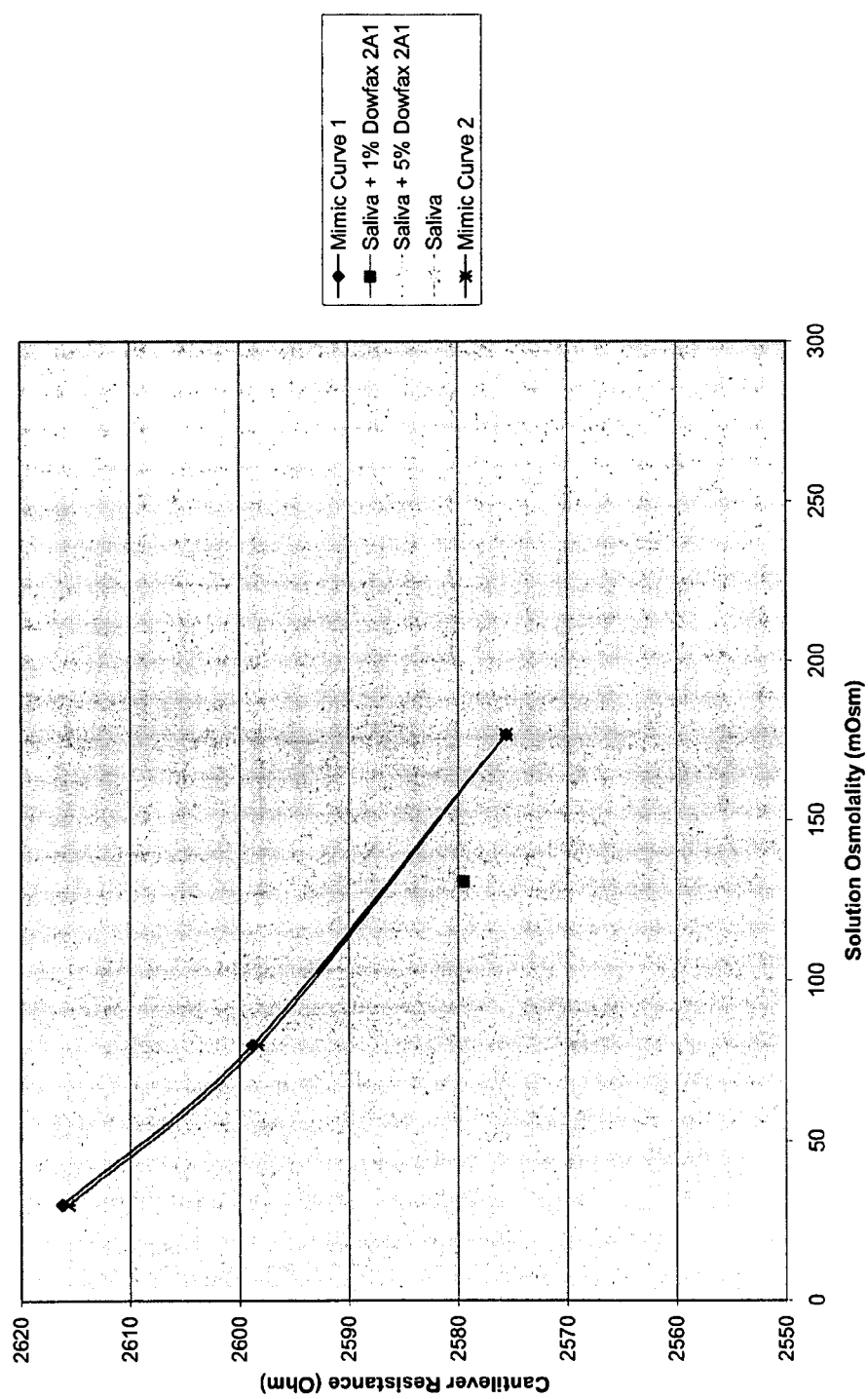
FIG. 7 is a graphic depiction of cantilever resistance (Ohms) versus solution osmolality (mOsm) for 2 NaCl solutions, untreated human saliva and human saliva samples treated with 1% or 5% Dowfax 2A1.

FIG. 7 provides a graphic depiction of cantilever resistance (Ohms) versus solution osmolality (mOsm) for 2 NaCl solutions (Mimic Curve 1 and Mimic Curve 2), untreated human saliva (Saliva) and human saliva samples treated with 1% Dowfax 2A1 (Saliva+1% Dowfax 2A1) or 5% Dowfax 2A1 (Saliva+5% Dowfax 2A1). The results indicate that Dowfax 2A1 treatment resulted in some improvement in the consistency of saliva osmolality when added to the saliva sample at a concentration of 1%, but not sufficiently to be of practical value.

Figure 8:
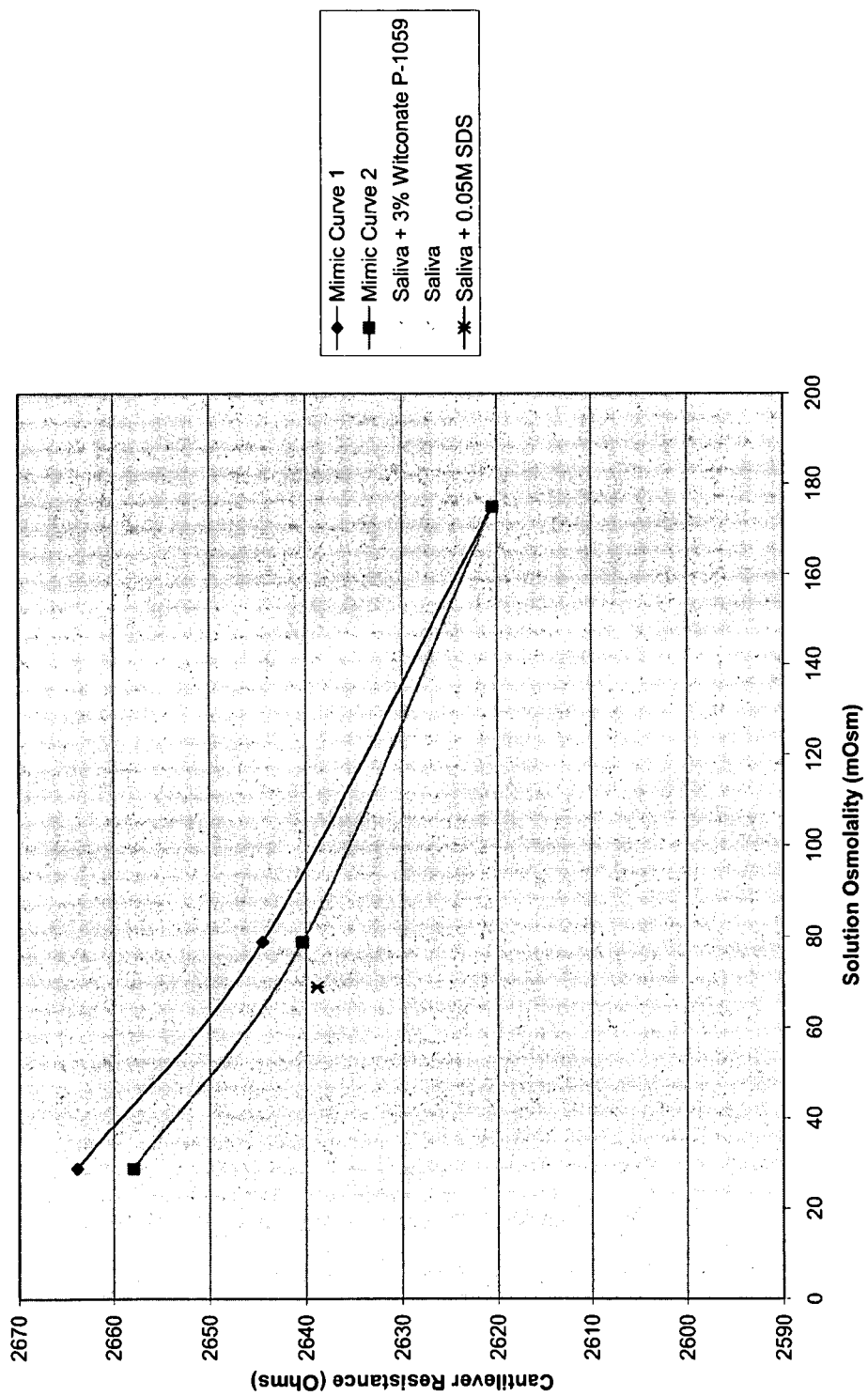
FIG. 8 is a graphic depiction of cantilever resistance (Ohms) versus solution osmolality (mOsm) for 2 NaCl solutions, untreated human saliva and human saliva samples treated with 3% Witconate P-1059.

FIG. 8 provides a graphic depiction of cantilever resistance (Ohms) versus solution osmolality (mOsm) for 2 NaCl solutions (Mimic Curve 1 and Mimic Curve 2), untreated human saliva (Saliva) and human saliva samples treated with 3% Witconate P-1059 (Saliva+3% Witconate P-1059) or 0.05M SDS (Saliva+0.05M SDS). The results indicate that Witconate P-1059 treatment resulted in some improvement in the consistency of saliva osmolality when added to the saliva sample at a concentration of 3%, but not sufficiently to be of practical value.

Example 2

MEASUREMENT OF OSMOLALITY OF SALIVA SAMPLES TREATED WITH SURFACTANTS

Further studies were carried out to test the effect of additional surfactants to determine if an accurate and consistent determination saliva osmolality could be achieved by sample treatment with surfactants prior to osmolality determination using a hydrogel sensor.

It was eventually determined that treatment of saliva with certain anionic surfactants resulted in accurate and consistent determinations saliva osmolality using hydrogel sensors as compared to freezing point depression.

Prior to carrying out the studies, sensing hydrogels were immersed in a dilute (0.05M) sodium hydroxide solution for one hour.

The results showed that treatment of saliva samples with SDS at a final concentration of from 0.01% to about 0.25% resulted in consistent and accurate values when saliva osmolality was measured using a hydrogel sensor.

Figure 9:
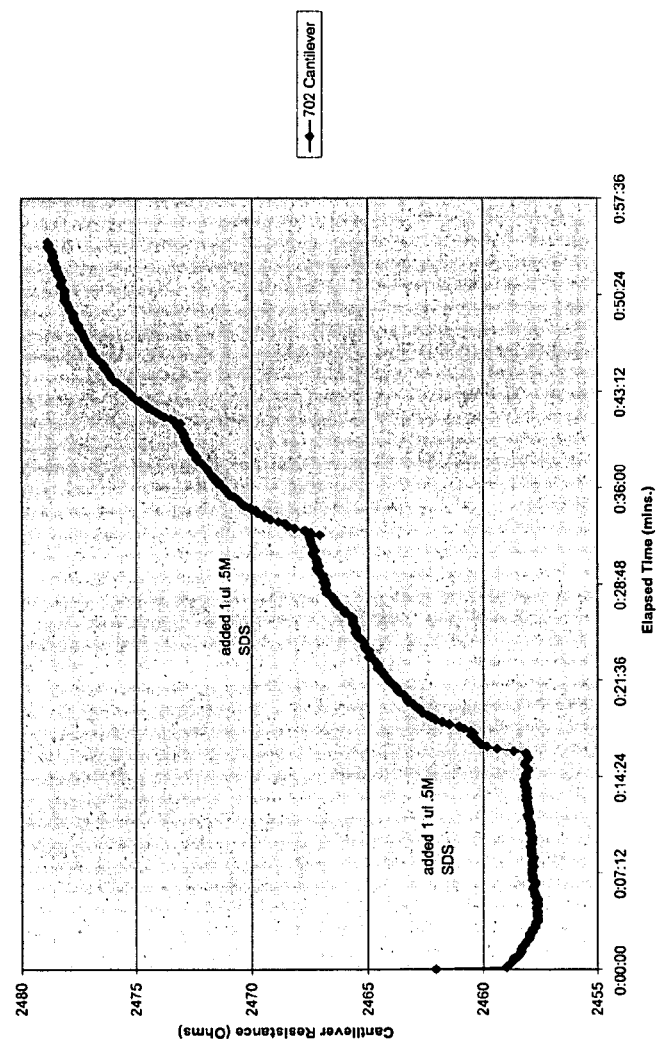
FIG. 9 is a graphic depiction of cantilever resistance (Ohms) versus time (mins.) for Cantilever 702 (702 Cantilever) wherein 0.5 M sodium dodecyl sulfate (SDS) was added to the sample at different time points.

FIG. 9 is a graphic depiction of cantilever resistance (Ohms) versus time for Cantilever 702 (702 Cantilever) wherein 1 microliter (ul) of 0.5 M SDS was added to a 1 mL of 90 mOsm saline solution at different time points. The results indicate increased swelling of the hydrogel versus time.

Figure 10:
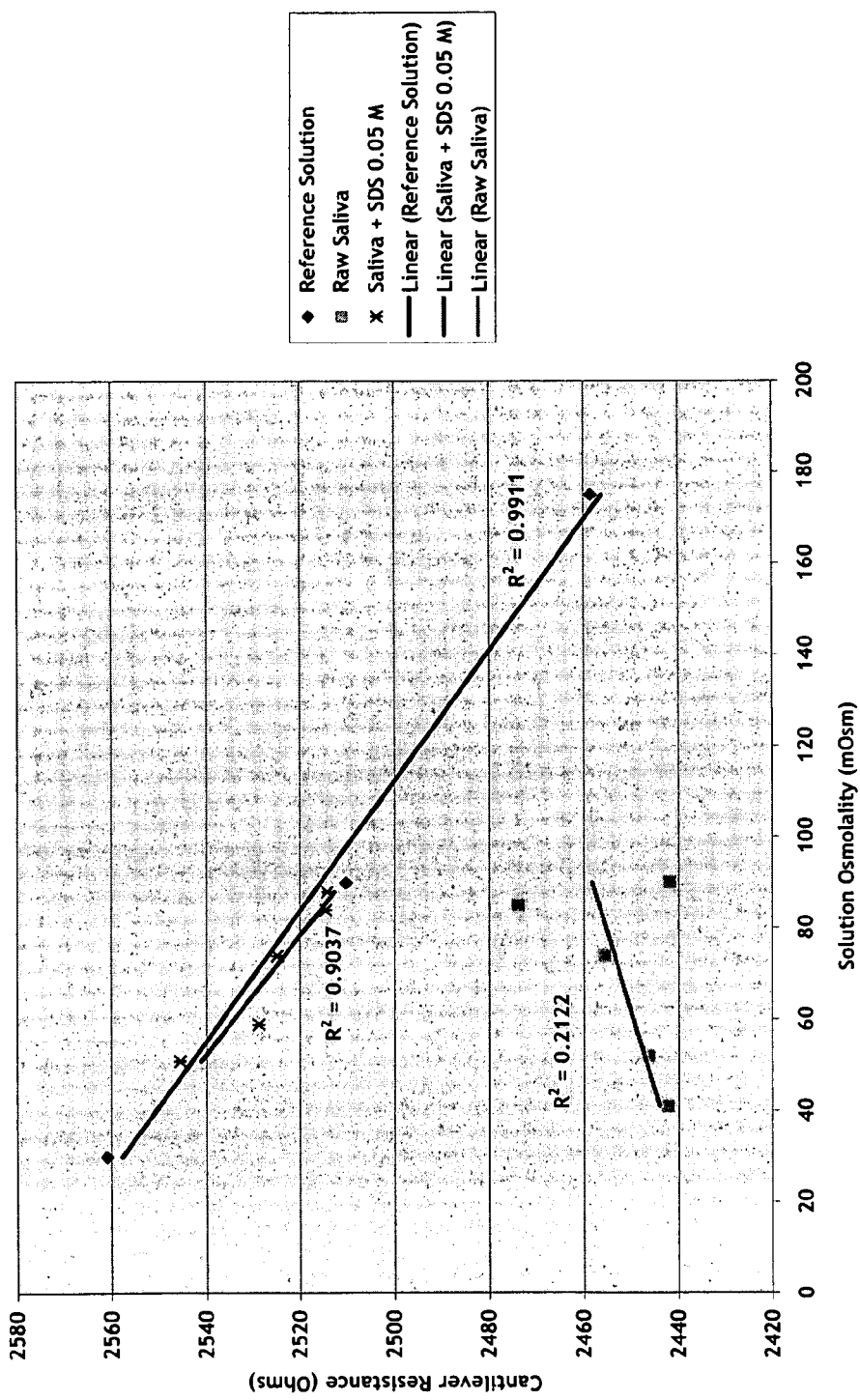
FIG. 10 is a graphic depiction of cantilever resistance (Ohms) versus solution osmolality (mOsm) for a reference NaCl solution, untreated (raw) human saliva and human saliva samples treated with 0.05M SDS.

FIG. 10 is a graphic depiction of cantilever resistance (Ohms) versus solution osmolality (mOsm) for a reference NaCl solution (Reference Solution), untreated human saliva (Raw Saliva) and human saliva samples treated with SDS wherein the final concentration of SDS in saliva was 0.05M. The results indicate that 0.05M SDS treatment of saliva resulted in consistent and accurate values when saliva osmolality was measured using a hydrogel sensor.

A solution of 0.5M 99.0% pure SDS (Bioworld) or Ultrapure SDS (J. T. Baker) was mixed into a 45 mOsm mimic NaCl solution through six serial dilutions, producing concentrations of approximately 0.5M, 0.25M, 0.125M, 0.063M, 0.031M, and 0.016M SDS. The osmolality of each solution, 45 mOsm mimic NaCl solution and the SDS solutions were tested on a Fiske 110 freezing point depression osmometer. Use of the Ultrapure SDS yielded more consistent results over the concentration range tested with a low level of interference while the 1% impurity in the Bioworld SDS solution yielded less consistent results at all concentrations tested (data not shown).

In another study, saliva samples from three human subjects were divided into individual aliquots and modified via addition of various quantities of SDS. The resulting saliva samples, along with unmodified controls, were tested using hydrogel sensors and a Fiske 110 freezing point depression osmometer. The sensor was cleaned in a low osmolality saline solution between samples, and the samples were in capped containers prior to measurement.

TABLE 2

Effect of Various Concentrations of SDS on Saliva Osmolality

| Surfactant/ Concentration | Saliva FPO (Freezing Point Osmolality) | Measured Osmolality (hydrogel sensor) | Difference |
|---|---|---|---|
| Saliva | 51 | 127 | 76 |
| Saliva | 67 | 132 | 65 |
| Saliva | 88 | 200 | 112 |
| Saliva | 67 | 149 | 82 |
| Saliva/0.01M SDS | 47 | 85 | 38 |
| Saliva/0.01M SDS | 66 | 90 | 24 |
| Saliva/0.01M SDS | 88 | 150 | 62 |
| Saliva/0.01M SDS | 66 | 91 | 25 |
| Saliva/0.03M SDS | 50 | 55 | 5 |
| Saliva/0.03M SDS | 64 | 67 | 3 |
| Saliva/0.03M SDS | 83 | 100 | 17 |
| Saliva//0.03M SDS | 64 | 76 | 12 |
| Saliva/0.05M SDS | 49 | 54 | 5 |
| Saliva/0.05M SDS | 65 | 68 | 3 |
| Saliva/0.05M SDS | 86 | 89 | 3 |
| Saliva//0.05M SDS | 65 | 67 | 2 |
| Saliva/0.07M SDS | 48 | 55 | 7 |
| Saliva/0.07M SDS | 62 | 67 | 5 |
| Saliva/0.07M SDS | 86 | 88 | 2 |
| Saliva//0.07M SDS | 62 | 67 | 5 |
| Saliva/0.09M SDS | 46 | 60 | 14 |
| Saliva/0.09M SDS | 58 | 67 | 9 |
| Saliva/0.09M SDS | 80 | 86 | 6 |
| Saliva//0.09M SDS | 58 | 67 | 9 |
| Saliva/0.1M SDS | 47 | 61 | 14 |
| Saliva/0.1M SDS | 63 | 70 | 7 |
| Saliva/0.1M SDS | 82 | 87 | 5 |

Table 2 shows that addition of SDS improved the accuracy, reliability and reproducibility of the response of hydrogel sensors in measurement of the osmolality of saliva. Optimal accuracy, reliability and reproducibility was evident for samples where the final concentration of SDS was between 0.03M and 0.1 M SDS.

Figure 11:
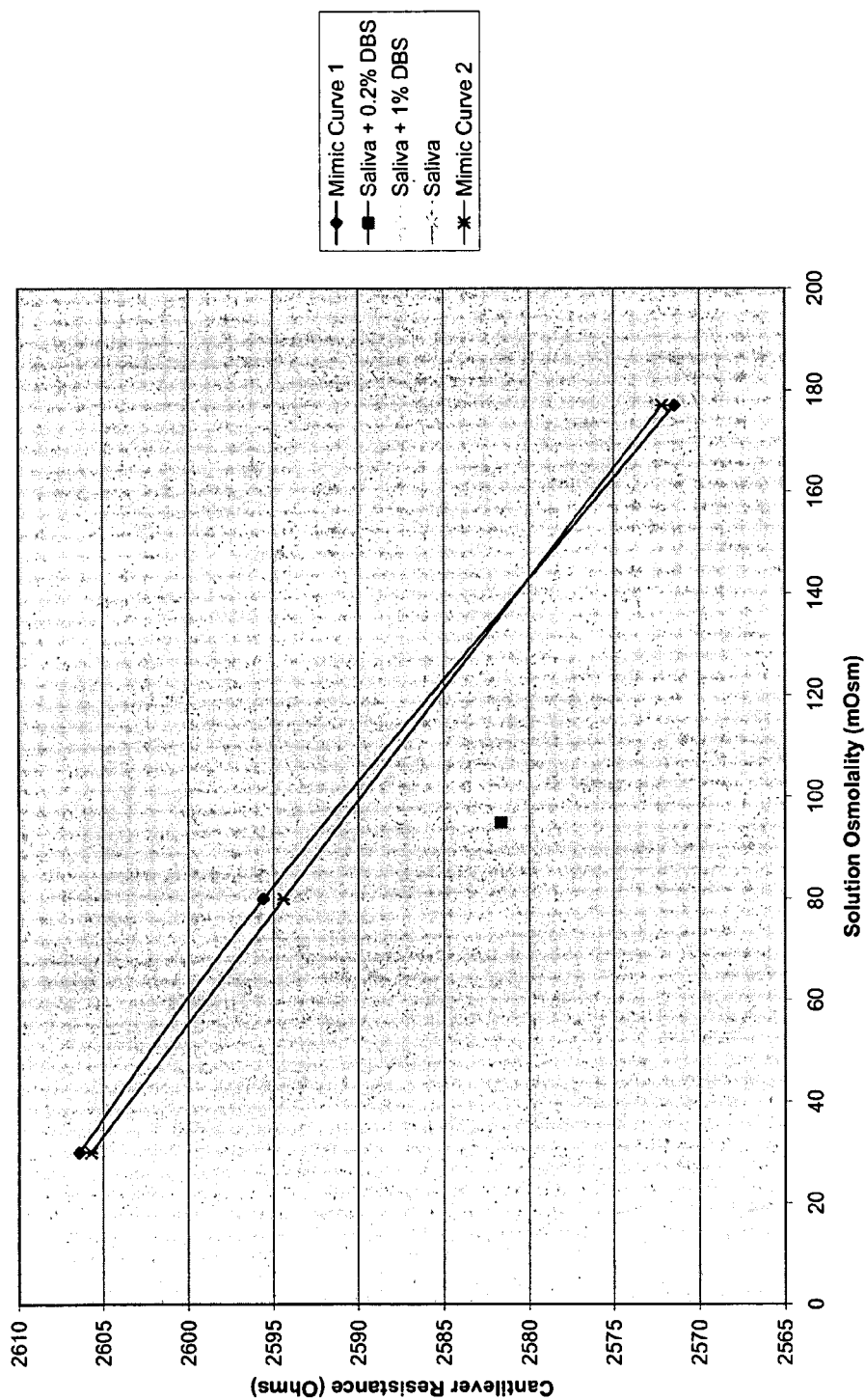
FIG. 11 is a graphic depiction of cantilever resistance (Ohms) versus solution osmolality (mOsm) for 2 NaCl solutions, untreated human saliva and human saliva samples treated with 0.2% or 1% dodecylbenzene sulfate (DBS).

FIG. 11 is a graphic depiction of cantilever resistance (Ohms) versus solution osmolality (mOsm) for 2 NaCl solutions (Mimic Curve 1 and Mimic Curve 2), untreated human saliva (Saliva) and human saliva samples treated with 0.2% DBS (Saliva+0.2% DBS) or 1% DBS (Saliva+1% DBS). The results indicate that 1% DBS treatment of saliva resulted in improved consistency and accuracy when saliva osmolality was measured using a hydrogel sensor.

Example 3

MEASUREMENT OF OSMOLALITY OF SALIVA SAMPLES TREATED WITH SURFACTANTS

In one experiment, a polymer was prepared using hydroxyl propyl acrylate, acrylamide and acrylic acid in a weight ratio of (85:14.5:0.5) and subsequently converted into a hydrogel by cross linking with 0.2% Cymel 327 (an aminoplast resin sold by Cytec Corporation). The hydrogel was incorporated into microcantilever based sensors and individual sensor response to temperature, pH and Osmolality was characterized, as shown in Table 3.

TABLE 3

Response of a Hydrogel Sensor to Temperature, Osmolality and pH.

| Sensor | Polymer Temp. Gain (ohm) 18° C. to 42° C. | Osmolality Gain (ohm) 30 to 175 mOsmol | pH Gain (ohm) pH 5.0 to 8.0 |
|---|---|---|---|
| 623 Rmc | −92 | 35 | 3.9 |
| 626 Rmc | −94 | 40.4 | −0.4 |
| 628 Rmc | −53.9 | 25.7 | 0.4 |
| 629 Rmc | −39.4 | 18.6 | 0.4 |
| 634 Rmc | −101.6 | 44.4 | 0.6 |
| 625 Rmc | −78.4 | 35.9 | 0.5 |
| 638 Rmc | −76.8 | 41.5 | 0.1 |
| 640 Rmc | −80.9 | 35.7 | 0 |
| 642 Rmc | −83 | 41.3 | 0 |
| 643 Rmc | −105.9 | 47.9 | −0.7 |

It will be appreciated that the temperature response of the sensors are in fact much higher than their sensitivity to osmolality or pH over the ranges of interest.

Figure 12:
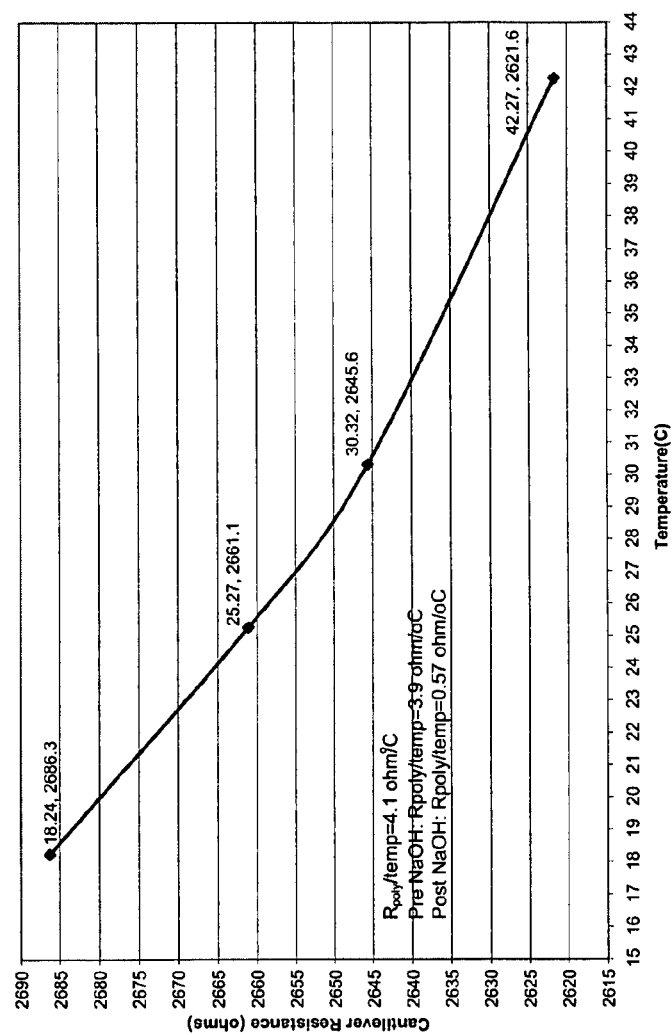
FIG. 12 is a graphic depiction of cantilever resistance (Ohms) versus temperature indicating hydrogel sensor response before and after treatment with NaOH.

In another test, sensors was prepared and characterized for temperature, osmolality and pH response. Subsequently the sensors were exposed to a 93 mosmol salt solution adjusted to pH 9.0 with sodium hydroxide for 4 hours followed by rinsing in a 30 mosmol salt solution for 24 hours. The sensors were then characterized again as shown in FIG. 12.

Before treatment the sensor had a temperature coefficient of about 3.9 ohm/degree C., while after treatment the temperature coefficient dropped to a out 0.57 ohm/degree C.

Surprisingly, the results show that sensitivity of the hydrogel sensor to osmolality increased after treatment with NaOH.

TABLE 4A

Before Treatment in NaOH

| Polymer | Sensor (build date) | Polymer Temp. (ohm) | Osm. Gain (ohm) | pH gain (ohm) | mucin gain (ohm) | Osm/ mucin | Osm/ polymer temp. | Osm/pH |
|---|---|---|---|---|---|---|---|---|
| BM23-69C | 649 Rmc (Dec. 21, 2006) | −55.3 | 50.7 | −3.5 | 14.2 | 3.6 | 0.9 | 14.5 |
| BM23-69C | 659 Rmc* (Dec. 29, 2006) | −60.1 | 54.8 | −4.4 | 17.7 | 3.1 | 0.9 | 12.5 |
| BM23-73C | 660 Rmc (Jan. 2, 2007) | −14.7 | 12.9 | −0.1 | −1 | −12.9 | 0.9 | 129.0 |
| BM23-73C | 662 Rmc (Jan. 2, 2007) | −78.3 | 11.9 | −15.3 | 4.4 | 2.7 | 0.2 | 0.8 |
| BM23-73D | 664 Rmc (Jan. 2, 2007) | −34.2 | 1.9 | −18.7 | −1.5 | −1.3 | 0.1 | 0.1 |
| BM23-73D | 665 Rmc (Jan. 2, 2007) | −23 | 16.3 | −7.1 | 3.6 | 4.5 | 0.7 | 2.3 |

*Sensor #659 was replaced by #688 which was built in Jan. 22, 2007

TABLE 4B

After Treatment in 0.025 NaOH

| Polymer | Sensor | Polymer Temp. (ohm) | Osm. Gain (ohm) | pH gain (ohm) | mucin gain (ohm) | Osm/ mucin | Osm/ polymer temp. | Osm/pH |
|---|---|---|---|---|---|---|---|---|
| BM23-69C | 649 Rmc (Dec. 21, 2006) | −27.3 | 123.4 | −0.7 | 8.4 | 14.7 | 4.5 | 176.3 |
| BM23-69C | 688 Rmc* (Dec. 29, 2006) | −25.9 | 117.5 | −0.2 | 36 | 3.3 | 4.5 | 587.5 |
| BM23-73C | 660 Rmc (Jan. 2, 2007) | −57.8 | 50.3 | −2.1 | 5.4 | 9.3 | 0.9 | 24.0 |
| BM23-73C | 662 Rmc (Jan. 2, 2007) | −78.7 | 44.8 | −6.3 | 8.6 | 5.2 | 0.6 | 7.1 |
| BM23-73D | 664 Rmc (Jan. 2, 2007) | −43.2 | 37.6 | −4.9 | 1.1 | 34.2 | 0.9 | 7.7 |
| BM23-73D | 665 Rmc (Jan. 2, 2007) | −39 | 36.1 | −0.1 | 4.1 | 8.8 | 0.9 | 361.0 |

TABLE 4C

Change before and after treatment in NaOH

| Polymer | Sensor | Change in Polymer Temp. (ohm) | Change in Osm. Gain (ohm) | Change in pH gain (ohm) | Change in mucin gain (ohm) | Change in Osm/mucin | Change in Osm/ polymer temp. | Change in Osm/pH |
|---|---|---|---|---|---|---|---|---|
| BM23-69C | 649 Rmc (Dec. 21, 2006) | 28.0 | 72.7 | 2.8 | −5.8 | 11.1 | 3.6 | 161.8 |
| BM23-73C | 660 Rmc (Jan. 2, 2007) | −43.1 | 37.4 | −2.0 | 6.4 | 22.2 | 0.0 | −105.0 |
| BM23-73C | 662 Rmc (Jan. 2, 2007) | −0.4 | 32.9 | 9.0 | 4.2 | 2.5 | 0.4 | 6.3 |
| BM23-73D | 664 Rmc (Jan. 2, 2007) | −9.0 | 35.7 | 13.8 | 2.6 | 35.4 | 0.8 | 7.6 |
| BM23-73D | 665 Rmc (Jan. 2, 2007) | −16.0 | 19.8 | 7.0 | 0.5 | 4.3 | 0.2 | 358.7 |

An FTIR scan showed that NaOH treatment of the hydrogel produces a carboxylate sodium salt. After treatment with NaOH, the emergence of a new peak at 1571 cm-1 was evident. This was attributed to the formation of the carboxylate sodium salt from ionization of the carboxylic acid groups. Washing with HCl (pH 1-2) to deionize the groups caused the peak to disappear. This result indicates that the sensing polymer is ionized by treatment with NaOH which increases the swelling (hydrophilic) characteristic of the hydrogel, which was reversed by treatment with HCl (pH 1-2).

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. A method for measuring a physical or chemical property of a biological fluid sample comprising biomolecules which interfere with a physical or chemical property of a hydrogel, comprising:
   treating a biological fluid sample with an anionic surfactant;
   contacting the anionic surfactant-treated biological fluid sample with a sensor comprising a hydrogel responsive by a change in a physical or chemical property to the biological fluid sample;
   by said treating, minimizing the effect of the interfering biomolecules on the hydrogel when said anionic surfactant-treated biological fluid sample is contacted with the sensor;
   evaluating a change in said physical or chemical property of said hydrogel in response to contact with said anionic surfactant-treated biological fluid sample; and
   correlating the change in said sensor with a physical or chemical property of said biological fluid sample.

2. The method according to claim 1, wherein said biological fluid is selected from the group consisting of saliva, whole blood, plasma, serum, tear fluid, lymph, synovial fluid, urine, sputum, semen, vaginal lavage, bone marrow and cerebrospinal cord fluid.

3. The method according to claim 2, wherein said biological fluid is saliva.

4. The method according to claim 1, wherein the change in said physical or chemical property of said hydrogel is a change in volume, a change in optical density, a change in refractive index or a change in AC conductivity.

5. The method according to claim 1, wherein said hydrogel is a cross-linked hydrogel having a net negative charge.

6. The method according to claim 5, wherein said hydrogel is a cross-linked hydrogel comprised of a hydroxyalkyl acrylate, a hydroxyalkyl methacrylate, a vinyl ether, or a vinyl pyrrolidone.

7. The method according to claim 1, wherein said hydrogel comprises an anionic moiety selected from a carboxylate group, a sulfate group, a sulfonate group and a phosphate group.

8. The method according to claim 1, wherein said anionic surfactant is selected from the group consisting of a fatty acid salt, an alkyl or alkyl aryl sulfate, sulfonate or sulfonic acid, a sulfoacetate, an alkyl or alkyl aryl phosphate, phosphate esters, dioctyl sulfosuccinates, alkyldiphenyloxide disulfonate salts, a sulfosuccinate, a lactylate, sodium dodecyl sulfate (SDS) and dodecylbezene sulfate (DBS).

9. The method according to claim 8, wherein a final concentration of said anionic surfactant is from about 0.01% to about 0.25% (w/w).

10. The method according to claim 8, wherein a final concentration of said anionic surfactant is from about 0.02% to about 0.15% (w/w).

11. The method according to claim 8, wherein said anionic surfactant is SDS and a final concentration is 0.03% to about 0.1% (w/w).

12. The method according to claim 8, wherein said anionic surfactant has a critical micelle concentration in water selected from the group consisting of less than 1%, less than 0.5% and less than 0.1% (w/w).

13. The method according to claim 8, wherein said SDS has less than 1% (w/w) of non surfactant impurities.

14. The method according to claims 1, wherein the physical or chemical property of said biological fluid sample is a physical property selected from the group consisting of absorption at a given wavelength, density, electric conductivity, pH, osmolality, osmolarity, thermal transfer, viscosity, dielectric constant, refractive index and light scattering.

15. The method according to claim 14, wherein said physical property is osmolality.

16. The method according to claims 1, wherein said physical or chemical property of said biological fluid sample is a chemical property selected from the group consisting of the concentration of glucose, creatinine, urea, cortisol, total protein, total electrolytes, estrogen, progesterone, testosterone, a cation, and an anion.

17. The method according to claim 16, wherein said cation is selected from the group consisting of sodium ($Na^+$); calcium ($Ca^{2+}$); potassium ($K^+$), and magnesium ($Mg^{2+}$).

18. The method according to claim 16, wherein said anion is selected from the group consisting of chloride ($Cl^-$), fluoride (Fl), bromide (Br), sulfate ($SO_4^{2-}$), nitrate ($NO_3^-$), carbonate ($CO_3^{2-}$), and bicarbonate ($HCO_3^-$).

19. The method according to claim 1, wherein said evaluating comprises monitoring said hydrogel for a decrease in volume to detect a saliva osmolality.

20. The method according to claim 1, wherein said evaluating comprises monitoring the hydrogel for an increase in hydrogel volume to detect saliva osmolality.

21. A method for measuring osmolality of a saliva biological sample, comprising:
   treating the saliva biological fluid sample with an anionic surfactant selected from sodium dodecyl sulfate (SDS) and dodecylbenzene sulfate (DBS);
   contacting the anionic surfactant-treated biological fluid sample with a sensor comprising a hydrogel responsive by a change in volume to the biological fluid sample;
   evaluating a change in volume of said hydrogel in response to contact with said anionic surfactant-treated saliva biological fluid sample; and
   correlating the change in said sensor with the osmolality of said saliva biological fluid sample.

* * * * *